United States Patent
Lara Sánchez et al.

(10) Patent No.: US 12,302,907 B2
(45) Date of Patent: May 20, 2025

(54) BACILLUS HALOSACCHAROVORANS STRAIN, COMPOSITION COMPRISING THE SAME, AND USES THEREOF

(71) Applicant: FUTURECO BIOSCIENCE, S.A., Olèrdola (ES)

(72) Inventors: José Manuel Lara Sánchez, Olèrdola (ES); Carolina Fernández Castillo, Olèrdola (ES)

(73) Assignee: FUTURECO BIOSCIENCE, S.A., Olèrdola (ES)

( * ) Notice: Subject to any disclaimer, the term of this patent is extended or adjusted under 35 U.S.C. 154(b) by 627 days.

(21) Appl. No.: 17/436,580

(22) PCT Filed: Mar. 5, 2020

(86) PCT No.: PCT/EP2020/055801
§ 371 (c)(1),
(2) Date: Sep. 3, 2021

(87) PCT Pub. No.: WO2020/178368
PCT Pub. Date: Sep. 10, 2020

(65) Prior Publication Data
US 2022/0142172 A1     May 12, 2022

(30) Foreign Application Priority Data
Mar. 5, 2019   (EP) ..................................... 19382164

(51) Int. Cl.
*A01N 63/22*    (2020.01)
*A01P 7/04*     (2006.01)
*C12N 1/20*     (2006.01)
*C12R 1/07*     (2006.01)

(52) U.S. Cl.
CPC ................ *A01N 63/22* (2020.01); *A01P 7/04* (2021.08); *C12N 1/205* (2021.05); *C12R 2001/07* (2021.05)

(58) Field of Classification Search
CPC ........... A01N 63/22; A01P 7/04; C12N 1/205; C12R 2001/07
See application file for complete search history.

(56) References Cited

FOREIGN PATENT DOCUMENTS

| | | |
|---|---|---|
| CN | 106187614 A | 12/2016 |
| CN | 106495827 A | 3/2017 |
| WO | WO 94/04684 A1 | 3/1994 |

(Continued)

OTHER PUBLICATIONS

Gadhave et al., Plant growth-promoting Bacillus suppress Brevicoryne brassicae field infestation and trigger density-dependent and density-independent natural enemy responses. 2016. J Pest Sci 89, p. 985-992. (Year: 2016).*

(Continued)

*Primary Examiner* — M Franco G Salvoza
*Assistant Examiner* — Naghmeh Nina Moazzami
(74) *Attorney, Agent, or Firm* — Squire Patton Boggs (US) LLP

(57) ABSTRACT

The present invention relates to a new isolated strain of the microorganism *Bacillus halosaccharovorans* which has nematicidal and insecticidal effect, the bacterial culture and the composition comprising it and their uses in the control of nematode and/or aphid infection in a plant. Also refers to a method to obtain the mutant strain of the invention.

13 Claims, 4 Drawing Sheets

Specification includes a Sequence Listing.

(56) References Cited

FOREIGN PATENT DOCUMENTS

WO    WO 2008/049230 A1    5/2008

OTHER PUBLICATIONS

Berlitz et al., Bacillus and Biopesticides in Control of Phytonematodes, 2014, Basic and Applied Aspects of Biopesticides, Springer, Chap 1, p. 3-16. (Year: 2014).*
Tijjani et al., Biopesticides for Pests Control: A Review, 2016, Journal of Biopesticides and Agriculture, vol. 3 No. 1, p. 6-13. (Year: 2016).*
English translation of CN106187614, provided by Espacenet. (Year: 2016).*
Stevenson, F., Lipids in soil, 1966, J Am Oil Chem Soc 43, 203-210. (Year: 1966).*
Yoon et al., A large-scale evaluation of algorithms to calculate average nucleotide identity, 2017, Antonie van Leeuwenhoek 110, 1281-1286 (Year: 2017).*
International Search Report and Written Opinion mailed Apr. 30, 2020 for International Application No. PCT/EP2020/055801, 16 pages.
Communication dated Jun. 4, 2019 forwarding the extended European Search Report for European Application No. 19382164.2, 7 pages.
Altschul, et al: "Basic local alignment search tool", Journal of Molecular Biology 1990; vol. 215, pp. 403-410; XP002949123; doi:10.1006/jmbi. 1990.9999.
Aubert, et al: "A Markerless Deletion Method for Genetic Manipulation of *Burkholderia cenocepacia* and Other Multidrug-Resistant Gram-Negative Bacteria", Methods in Molecular Biology 2014; vol. 1197, pp. 311-327.
Hemraj, et al. 2013 "A review on commonly used biochemical test for bacteria" Innovare Journal of Life Science 2013; vol. 1(1), pp. 1-7.
Higgins, et al.: "Clustal V: improved software for multiple sequence alignment", CABIOS 1992; vol. 8(2), pp. 189-191; XP008137000.
Richter, et al.: "JSpeciesWS: a web server for prokaryotic species circumscription based on pairwise genome comparison", Bioinformatics; Nov. 16, 2015; vol. 32(6), pp. 929-931.
Sambrook, et al: "Molecular Cloning—A Laboratory Manual / Chapter 13, Mutagenesis", Cold Spring Harbor Laboratory Press, 3rd Edition, 2001.
Stoddard, et al: "*rrn*DB: improved tools for interpreting rRNA gene abundance in bacteria and archaea and a new foundation for future development", Nucleic Acids Research 2015 (online Nov. 20, 2014); vol. 43; Database issue D593-D598.
Xiang, et al: "Biological control of *Meloidogyne incognita* by Spore-forming Plant Growth-promoting Rhizobacteria on Cotton", Plant Disease 2017; vol. 101(5), pp. 774-784.
XP 002798603.
XP 002798604.
XP 002798605.

* cited by examiner

BACILLUS HALOSACCHAROVORANS STRAIN, COMPOSITION COMPRISING THE SAME, AND USES THEREOF

CROSS-REFERENCE TO RELATED APPLICATION

This application is a U.S. national phase entry of International Patent Application No. PCT/EP2020/055801, filed Mar. 5, 2020, which claims priority to European Patent Application EP19382164.2 filed on Mar. 5, 2019. The contents of both related applications are incorporated herein by reference in their entirety.

INCORPORATION BY REFERENCE TO SEQUENCE LISTING SUBMITTED

This application contains a sequence listing entitled "108663_00281_SEQLISTING.txt," being submitted herein in ASCII format via EFS-Web, which is a copy of the sequence listing as filed in the PCT/EP2020/055801, which was renamed on Sep. 1, 2021 and is 2,942 bytes in size.

TECHNICAL FIELD

The present invention relates to the field of phytosanitary products. It provides a new isolated strain of the microorganism *Bacillus halosaccharovorans*, compositions comprising it and their use in the biological control of diseases caused by parasitic nematode and aphids in plants.

BACKGROUND ART

Plant-parasitic nematodes and insects cause economically significant damage in crops and horticultural crops, and significantly reduce agricultural yields and diminish the harvests in case they are not eradicated.

Plant-parasitic nematodes infect the root system of crop plants, such as potato, sugar beet and tomato crops. Parasitic nematodes include root-knot nematodes, for example, *Meloidogyne* genus; cyst nematodes for example, *Globodera* genus; and root-lesion nematodes, for example, *Pratylenchus* genus.

Aphids, which are piercing-sucking insects, ingest plant sap by inserting their mouthparts therein (into the stalk, leaf or roots). They attack almost all plant species. The damage can be seen in the form of yellowish mottled discolorations which normally appear on the underside of leaves which subsequently dry out and die. Some aphid species form galls or cause leaves to coil or become deformed. Aphids established on other parts of the plant, such as stalks or branches, may delay growth, cause rapid leaf loss or branch death. Aphids are also carriers of numerous viral diseases.

The most commonly used nematode and aphid management strategy is chemical control but, although is effective, it may lead to soil pollution problems, affecting biodiversity and having a negative impact on human health.

Over the last decades, researchers have tried to develop non-chemical and ecofriendly approaches. Related to the control of plant nematodes, it has been reported the nematicidal activity of certain bacterial strains against *Meloidogyne incognita*, (for example, Xiang N at al. "Biological control of *Meloidogyne incognita* by Spore-forming Plant Growth-promoting Rhizobacteria on Cotton" Plant Disease 2017(101):774-784). Commercial products for controlling plant nematodes comprising bacteria from the *Bacillus* genus have been developed, for example: BioNem-WP/BioSafe (*B. firmus*), BioYield (*B. velezensis* and *B. subtilis*); Nemix (*Bacillus* spp.), VOTiVO® (*B. firmus*) and Pathway Consortia (*B. subtilis, B. licheniformis, B. megaterium, B. coagulans, Pseudomonas fluorescens, Streptomyces* spp., and *Trichoderma* spp.). Unfortunately, the nematicidal effect reported in the prior art, using bacterial strains, is limited to particular crop plants and to particular parasitic nematodes.

Certain bacteria have also been used against members of the Aphididae family, for example by using *Bacillus thuringiensis* aphidicidal toxins or transgenic plants comprising said toxins (WO9404684).

It is important to point out that the environmental aid host conditions affect the biological activity of the bacteria strains, making their effectiveness generally variable ad significantly lower than the reference chemical products.

In spite of the efforts made, therefore, there is a need for bacterial strains with a broad action spectrum against nematodes and aphids.

SUMMARY OF THE INVENTION

The inventors have surprisingly found one strain of the *Bacillus halosaccharovorans* species (hereinafter also referred as "bacterial strain B410") which is a pesticide with activity is against plait-parasitic nematodes, such as root-knot nematodes and cyst nematodes, but also against aphid insects.

As it is shown below, the strain of the invention has been tested in growth chamber and greenhouse trials ad has demonstrated to be efficient, in terms of nematode control, against the root-knot nematodes (RKNs) *Meloidogyne incognita* and *Meloidogyne javanicus* in tomato plants and against the potato cyst nematodes (PCNs) *Globodera rostochiensis* and *Globodera pallida*. It is remarkable that the in vitro efficacy of the strain of the invention against the tested nematodes, in terms of on RKN egg hatching inhibition, was better than the one achieved using the reference nematicidal chemical Oxamyl (FIG. 2) or similar to the one achieved with another reference nematicidal chemical, Fenamiphos (FIG. 1). In juveniles of RKN, the in vitro efficacy in terms of survival was similar than the efficacy presented by Fenamiphos (FIG. 3).

This anti-nematode effect was also detected in vivo, in terms of nematode control measuring final population of eggs per plant and RKN reproduction. This was achieved using the bacteria of the invention in several forms: as pellet (example 5.1), as Technical Grade Active Ingredient (TGAI) (example 5.2) and as formulated prototype (oil dispersion) (example 5.3).

In relation to potato cyst nematodes, the bacterial strain of the invention also showed percentage of inhibition of egg hatching of nearly 100% at the end of the treatment (FIGS. 4 and 5).

In addition to the anti-nematode effect, the strain of the invention has also shown to be effective as insecticide against the aphid *Aphis gossypii*. As it is shown below, the strain B410 achieved significant mortality of the aphid *Aphis gossypii* acting as TGAI (FIGS. 6 and 7).

From these experimental data it could be concluded that the bacterial strain of the present invention has a dual effect controlling nematodes and Aphids. This is the first time that it is reported a strain of *B. halosaccharovorans* with such particular double effect. Furthermore, it is surprising that it has a better effect in comparison with a reference chemical in vitro.

In addition, to such remarkable activity profile, it was also found that the strain of the present invention did not present acute oral toxicity in mice. The results showed that animals had no visible clinical adverse effects and no infectivity of pathogenicity was found.

The inventors have found further that the identified strain was mesophyll, neutrophil, halotolerant and a strong biofilm producer. Halotolerant microorganisms are of considerable agriculture interest because can be applicable to areas such as arid-zone agriculture areas and could be increased the agricultural productivity of lands affected by soil salination or where only saline water is available. In addition, many environmental stressors involve or induce osmotic changes; therefore, halotolerance is an advantageous characteristic. B410 is a strong biofilm producer, an important characteristic during microbial colonization and survival in unfavorable environments.

Therefore, the strain of the present invention benefits the growth of the bacterized plant.

The use of the strain of the present invention for controlling a nematode and/or insect infection is environmentally friendly.

Altogether the strain of the present invention means a get advance in the field of biopesticides.

Thus, the first aspect of the present invention refers to a strain of *Bacillus halosaccharovorans* deposited at the "Colección Española de Cultivos Tipo" (CECT) under the accession number CECT9165, or a mutant thereof, wherein said mutant is obtained using the CECT9165 of *Bacillus halosaccharovorans* as starting material and maintains the nematicidal effect and aphidicidal effect of CECT9165.

In the present invention the terms "B410" and "CECT9165", referring to the strain of the invention, are used interchangeably.

The strain of the invention was isolated from an agricultural soil in Almeria (Spain) and was deposited, according to the Budapest Treaty, at the CECT in the Edificio 3 CUE, Parc Cientific Universidad de Valencia C.P 46980 Catedrático Agustín Escardino No 9 Paterna, Valencia (Spain), under the accession number CECT9165. It was deposited by the depositor Futureco Bioscience S.A., Av. Del Cadi 19-23 P.I. Sant Pere Molanta 08799 Olèrdola Barcelona, on the 13 Jul. 2016. The strain was identified by the depositor with the reference B410, and received the accession number CECT9165. It was, in addition, declared viable.

A second aspect of the present invention refers to a bacterial culture comprising the strain as defined in the first aspect of the invention.

Due to the pesticidal effect of the strain of the present invention, it can be used as a phytosanitary product. As it is illustrated in the examples below, the strain of the first aspect of the invention can be used as a phytosanitary product according to FAO guidelines, which are the guidelines emitted by Food and Agriculture Organization of the United Nations. The isolated bacteria as defined in the first aspect of the invention may be used as ingredient of a phytosanitary composition.

Therefore, a third aspect of the present invention refers to a composition comprising an effective amount of the strain as defined in the first aspect of the invention, or the bacterial culture as defined in the second aspect of the invention, and one or more agriculturally acceptable compound(s).

A fourth aspect of the invention refers to a method to obtain a mutant of the strain of CECT9165 of *Bacillus halosaccharovorans*, comprising using the deposited strain as starting material and applying mutagenesis, wherein the obtained mutant maintains the activity of the parent deposited strain of controlling a plant nematode and an aphid infection in a plant.

A fifth aspect of the invention refers to a process for obtaining a viable cell suspension derived from the strain CECT9165 of *B. halosaccharovorans*, or a mutant thereof, of the first aspect of the invention; the process comprising: (i) inoculating the strain in a culture medium, (ii) subjecting the inoculated culture medium of the step (i) to conditions suitable for growth of the strain, and (iii) optionally subjecting the medium resulting from step (ii) to a concentration step.

The dual activity against plant-parasitic nematodes and aphids showed by the *B. halosaccharovorans* strain B410 could be extrapolated to other strains of *B. halosaccharovorans*.

Therefore, a sixth aspect of the invention refers to use of an isolated strain of *Bacillus halosaccharovorans*, which has nematicidal and insecticidal effect, for controlling a nematode and/or an insect infection in a plant.

A seventh aspect of the present invention refers to a method for controlling an infection caused by nematodes and/or insects in a plant comprising applying to a part of a plant or to the substrate used for growing said plant a strain of *Bacillus halosaccharovorans* which has nematicidal and insecticidal effect.

An eighth aspect of the present invention relates to a kit that comprises an effective amount of the strain of the first aspect of the invention, or the bacterial culture of the second aspect of the invention or the composition of the third aspect of the invention.

A ninth aspect of the present invention relates to the use of the kit of the eighth aspect of the invention for controlling of a nematode infection and/or an aphid infection in a plant.

Figure 1:
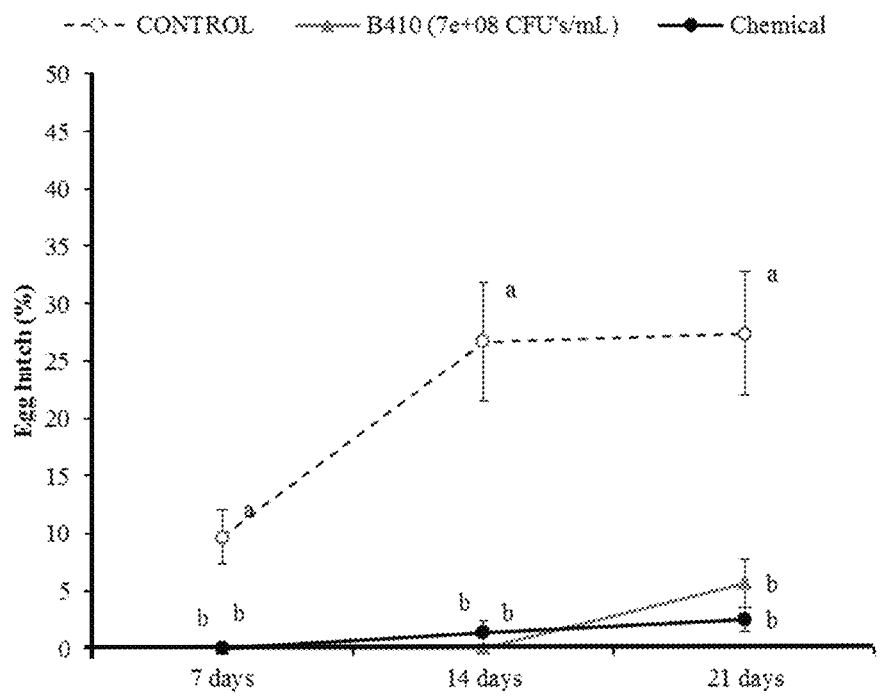
FIG. 1 shows a comparison of the in vitro nematicidal activity of *B. halosaccharovorans* strain B410 and Nemacur® ("chemical") against eggs of *Meloidogyne javanica* and *M. incognita*.

In all the figures: data represented with different letter ("a" or "b") indicate that there was a statistically significant difference among them (data were subjected to analysis of variance (ANOVA) using a R program; treatment means were compared using Fisher's protected least significant difference test (LSD) at $P=0.05$). "Control": negative control. "Egg hatch (%)": percentage of egg hatching.

DETAILED DESCRIPTION OF THE INVENTION

All terms as used herein in this application, unless otherwise stated, shall be understood in their ordinary meaning as known in the art. Other more specific definitions for certain terms as used in the present application are as set forth below and are intended to apply uniformly throughout the specification and claims unless an otherwise expressly set out definition provides a broader definition. The definitions given herein are included for the purpose of understanding and expected to be applied throughout description, claims and drawings.

The first aspect of the invention refers to an isolated strain of *Bacillus halosaccharovorans* deposited at the "Colección Española de Cultivos Tipo" (CECT) under the accession number CECT9165, or a mutant thereof, wherein said mutant strain is obtained using the CECT9165 of *Bacillus halosaccharovorans* and maintains both the nematicidal effect and aphidicidal effect of CECT9165.

In a particular embodiment of the first aspect of the invention, optionally in combination with any of the embodiments provided below, the isolated strain of *Bacillus halosaccharovorans* is the *B. halosaccharovorans* strain B410 deposited at the "Colección Española de Cultivos Tipo (CECT)" under the accession number CECT9165.

In another embodiment of the first aspect of the invention, the strain is a mutant of the strain CECT9165 which maintains the nematicidal and aphidicidal effect of the starting strain.

The term "mutant" of the strain CECT9165 is also understood according to the invention as a "variant" of the strain CECT9165.

By using the deposited strain as starting material, the skilled person in the art can routinely, by genetic engineering techniques such as mutagenesis or bacterial recombination techniques, obtain mutants that maintain the herein described relevant features and advantages of the strain of the invention. In an embodiment of the invention, the mutant is a genetically modified mutant obtained by random mutagenesis (i.e. using chemical or physical agents) or by site-directed mutagenesis, combinatorial mutagenesis or insertional mutagenesis. In another embodiment of the first aspect of the present invention, the mutant is obtained by using recombinant technology, for example using transformation (for example, by electroporation, heat-shock or using divalent cation solutions, such as calcium chloride), transduction or conjugation techniques. By using recombinant technology a plasmid can be included in the bacterial strain; said plasmid can comprise antibiotic resistant genes or genes that serve for the selection of the mutant. Examples of genetic engineering techniques can be found in Sambrook, J. and Russell, D. W. "Molecular Cloning: A Laboratory Manual", Chapter 13, "Mutagenesis", Cold Spring Harbor, 3rd Ed, 2001.

As mentioned above, the mutant provided by the present invention has to maintain the dual effect shown by the strain CECT9165, i.e., the anti-nematode and anti-aphid activities. In the present invention the term "maintain", when referred to the mutant, means that it has to display both the anti-nematode and anti-aphid activity. Of course, as a consequence of the mutation in the strain, the resulting mutant encompassed by the present invention can display both activities more efficiently than the strain CECT9165.

In order to determine whether the mutant maintains the dual profile as anti-nematode and anti-aphid, several well-known protocols can be followed. These methods are commonly based on the analysis of the growth capacity of the pathogen in contact with the strain, or the assessment of the severity of the disease caused by the pathogen infection after the exposition to the strain. The protocols that are included in the examples herein for the determination of the activity are illustrative and non-limitative examples. Briefly, they are based on in vitro nematode egg-hatching and nematode survival; and in vivo nematode reproduction analysis.

In another embodiment of the first aspect of the invention, optionally in combination with any of the embodiments provided above or below, the mutant of the strain CECT9165 of *Bacillus halosaccharovorans* has a genomic sequence identity of at least 99.8% (99.8% or 99.9%) with the strain CECT9165 of *Bacillus halosaccharovorans*.

In the present invention the term "identity" refers to the percentage of residues that are identical in the two sequences when the sequences are optimally aligned. If, in the optimal alignment, a position in a first sequence is occupied by the same amino acid residue as the corresponding position in the second sequence, the sequences exhibit identity with respect to that position. The level of identity between two sequences (or "percent sequence identity") is measured as a ratio of the number of identical positions shared by the sequences with respect to the size of the sequences (i.e., percent sequence identity=(number of identical positions/total number of positions)×100).

A number of mathematical algorithms for rapidly obtaining the optimal alignment and calculating identity between two or more sequences are known and incorporated into a number of available software programs. Examples of such programs include the MATCH-BOX, MULTAIN, GCG, FASTA, and ROBUST programs for amino acid sequence analysis, among others. Preferred software analysis programs include the ALIGN, CLUSTAL W, and BLAST programs (e.g., BLAST 2.1, BL2SEQ, and later versions thereof).

For amino acid sequence analysis, a weight matrix, such as the BLOSUM matrixes (e.g., the BLOSUM45, BLOSUM50, BLOSUM62, and BLOSUM80 matrixes), Gonnet matrixes, or PAM matrixes (e.g., the PAM30, PAM70, PAM120, PAM160, PAM250, and PAM350 matrixes), can be used in determining identity.

The BLAST programs provide analysis of at least two sequences, either by aligning a selected sequence against multiple sequences in a database (e.g., GenSeq), or, with BL2SEQ, between two selected sequences. BLAST programs are preferably modified by low complexity filtering programs such as the DUST or SEG programs, which are preferably integrated into the BLAST program operations. If gap existence costs (or gap scores) are used, the gap existence cost preferably is set between about −5 and −15. Similar gap parameters can be used with other programs as appropriate. The BLAST programs and principles underlying them are further described in, e.g., Altschul at al., "Basic local alignment search tool", 1990, J. Mol. Biol, v. 215, pages 403-410.

For multiple sequence analysis, the CLUSTAL W program can be used. The CLUSTAL W program desirably is run using "dynamic" (versus "fast") settings. Sequences we evaluated using a variable set of BLOSUM matrixes depending on the level of identity between the sequences. The CLUSTAL W program and underlying principles of operation are further described in, e.g., Higgins at al., "CLUSTAL V: improved software for multiple sequence alignment", 1992, CABIOS, 8(2), pages 189-191.

In another embodiment of the first aspect of the invention, optionally in combination with any of the embodiments provided above or below, the mutant of the strain CECT9165 of *Bacillus halosaccharovorans*, has an average nucleotide identity (ANI) of at least 99.8% (99.8% or 99.9%) with the strain CECT9165 of *Bacillus halosaccharovorans*.

In another embodiment of the first aspect of the invention, optionally in combination with any of the embodiments provided above or below, the method to determine the ANI of the mutant of the invention is the method "ANIm" described in Richter M, et al. 2015 JSpeciesWS: a web server for prokaryotic species circumscription based on pairwise genome comparison. Bioinformatics. 2015 Nov. 16. pii: btv681.

In another embodiment of the first aspect of the invention, optionally in combination with any of the embodiments provided above or below, the method to obtain a mutant of the strain of the invention, for example with a genomic sequence identity of at least 99.8% with the strain CECT9165 of *Bacillus halosaccharovorans* are the mutagenic methods described in Aubert et al., "A Markerless Deletion Method for Genetic Manipulation of *Burkholderia cenocepacia* and Other Multidrug-Resistant Gram-Negative Bacteria" Methods Mol Biol 2014; 1197:311-27.

In a particular embodiment of the first aspect of the invention, optionally in combination with any of the embodiments provided above or below, the nematicidal effect is against at least a nematode of the genus *Meloidogyne* and *Globodera*. In another embodiment, the nematicidal effect is against one or more of *Meloidogyne incognita*, *Meloidogyne javanica*, *Globodera rostochiensis* and *Globodera pallida*. In another embodiment, the strain as defined in the first aspect of the invention has a nematicidal effect against *Meloidogyne incognita*, *Meloidogyne javanica*, *Globodera rostochiensis* and *Globodera pallida*.

In a particular embodiment of the first aspect of the invention, optionally in combination with any of the embodiments provided above or below, the strain as defined in the first aspect of the invention has an insecticidal effect at least against the Aphidoidea superfamily. In another embodiment, optionally in combination with any of the embodiments provided above or below, the strain as defined in the first aspect of the invention has an insecticidal effect at least against the Aphididae family. In another embodiment, the strain as defined in the first aspect of the invention has an insecticidal effect against *Aphis gossypii*.

In another embodiment of the first aspect of the invention, optionally in combination with any of the embodiments provided above or below, the strain as defined in the first aspect of the invention has a nematicidal effect against *Meloidogyne incognita*, *Meloidogyne javanica*, *Globodera rostochiensis* and *Globodera pallida*; and an aphidicidal effect is against *Aphis gossypii*.

A second aspect of the invention refers to a bacterial culture comprising the strain as defined in the first aspect of the invention.

In an embodiment of the second aspect of the invention, the bacterial culture comprises a viable strain as defined in the first aspect of the invention.

In another embodiment of the second aspect of the invention, the bacterial culture comprises the strain of the invention inactivated.

The term "inactivated" means that the micro-organism is not able to form colonies. In one embodiment, the inactivated micro-organisms have the cell membrane intact or broken.

In an embodiment of the second aspect of the invention, the bacterial culture is an inoculation product.

By "inoculation product" it is understood a product obtained after inoculating the strain in a suitable culture medium, subjecting the inoculated culture medium to suitable growth conditions.

In another embodiment of the second aspect of the invention, the inoculation product comprising the strain of the invention inactivated.

By "inoculation product comprising the strain of the invention inactivated" refers to a product obtained after inoculating the strain in a suitable culture medium, subjecting the inoculated culture medium to suitable growth conditions, and then inactivating the strain.

With a view to practical use in pest control, pesticide agents are usually formulated into compositions also including agriculturally acceptable compounds. Therefore, a third aspect of the present invention refers to a composition comprising an effective amount of the strain as defined in the first aspect of the invention, or the bacterial culture as defined in the second aspect of the invention, and one or more agriculturally acceptable compounds.

The term "effective amount" as used herein, means an amount of an active agent (ingredient; i.e., a bacterial strain, in the present invention is the strain *B. halosaccharovorans* CECT9165 or a mutant thereof) high enough to deliver the desired benefit, the control of nematodes and aphids, but low enough to avoid serious side effects.

In an embodiment of the third aspect of the invention, optionally in combination with any of the embodiments provided above or below, the strain is present at a concentration from $10^5$ cfu/ml to $10^{12}$ cfu/ml. In another embodiment of the third aspect of the invention, the strain is present at a concentration of $10^5$ cfu/mL, $10^6$ cfu/mL, $10^7$ cfu/mL $10^8$ cfu/mL, $10^9$ cfu/mL, $10^{10}$ cfu/mL, $10^{11}$ cfu/mL or $10^{12}$ cfu/mL.

For the purposes of the invention, any ranges given include both the lower and the upper end-points of the range.

The amount indicated as cfu/dose relates to the colony forming units (CFU) of the strain of the invention per dose. The amount indicated as cfu/mL relates to the colony forming units of the strain of the invention per milliliter.

The term "effective amount" as used herein, means an amount of the strain *B. halosaccharovorans* CECT9165 as defined in the first aspect of the invention, high enough to provide the desired benefit, either the treatment or prevention of the plant disease, but low enough to avoid serious side-effects. The particular dose of compound administered according to this invention will of course be determined by the particular circumstances surrounding the case, including the compound administered, the route of administration, the particular condition being treated, and the similar considerations.

In another embodiment of the third aspect of the invention, optionally in combination with any of the embodiments provided above or below, the composition is a phytosanitary composition.

In another embodiment of the third aspect of the invention, optionally in combination with any of the embodiments provided above or below, the agriculturally acceptable compound is selected from the group consisting of: plant strengtheners, nutrients, wetting agents, compounds that improve adherence, buffering compounds, stabilizers, antioxidants, osmotic protectors and sunscreens.

In another embodiment of the third aspect of the invention, optionally in combination with any of the embodiments provided above or below, the composition comprises at least one additional pesticide.

In another embodiment of the third aspect of the invention, optionally in combination with any of the embodiments provided above or below, the additional pesticide is selected from the group consisting of another bacterial strain with pesticide properties, a fungicide, a bactericide, an herbicide, a chemical insecticide or a chemical nematicide. Said additional pesticide does not have to adversely affect the activity/viability of the strain of the invention included in the composition.

In the present invention, the term "pesticide" is understood by its usual meaning in the field of agronomy as a product intended to kill, repel, regulate or disrupt the growth of living organisms that are considered pests. Clearly, due to the nature of the strain CECT9165 of *B. halosaccharovorans* or of the mutant thereof, herein it is understood that "pesticide" is a biological or ecological (organic) pesticide, also called biopesticide. In the scope of the present invention, the term "pesticide" would have the same meaning as the term "phytosanitary".

In an embodiment of the third aspect of the invention, optionally in combination with any of the embodiments provided above or below, it can be in the form of a solution, a pellet, a suspension, a lyophilized compositions or other dried compositions (for example freeze dried composition). The lyophilized or dried composition can be reconstituted with a liquid carrier prior to its use or directly used. The composition may be prepared according to various formulations suitable for phytosanitary uses, for example, chosen from the group consisting of formulations of the following type: liquid intended for use without dilution (AL), powder intended for use without dilution (AP), encapsulated granule (CG), contact liquid or gel (CL), contact powder (CP), powdering powder (DP), emulsifiable concentrate (EC), emulsifiable granule (EG), oil type emulsion (EO), water type emulsion (EW), fine granule (FG), macrogranules (GG), emulsifiable gel (GL), powder for spraying (GP), granules (GR), grease (GS), water-soluble gel (GW), microemulsion (ME), microgranules (MG), water-dilutable concentrated suspension (OF), oil dispersion (OD), water-miscible suspension (OL), powder for dispersion in oil (OP), concentrated in gel or paste form (PC), sticks (for agripharmaceutical use) (PR), concentrated suspension (SC), suspoemulsion (SE), water-soluble granules (DG), soluble concentrate (SL), fin-forming oil (SO), water-soluble powder (SP), water-soluble tablets (ST), tablets (TB), water-dispersible granules (WG), wettable powder (WP), water-cispersible tablets (WT) (the code consisting of two capital letters corresponding to the international codes for phytosanitary formulations).

In an embodiment of the third aspect of the invention, optionally in combination with any of the embodiments provided above or below, the composition is an oil dispersion (OD) composition.

In an embodiment of the third aspect of the invention, optionally in combination with any of the embodiments provided above or below, the composition is an OD formulation and comprises a concentration of the strain as defined in the first aspect of the invention in the range from $10^5$ to $10^{12}$ CFU/mL ($10^5$ cfu/mL, $10^6$ cfu/mL, $10^7$ cfu/mL $10^8$ cfu/mL, $10^9$ cfu/mL, $10^{10}$ cfu/mL, $10^{11}$ cfu/mL or $10^{12}$ cfu/mL).

In an embodiment of the third aspect of the invention, optionally in combination with any of the embodiments provided above or below, the composition is an OD formulation and comprises a concentration of the strain as defined in the first aspect of the invention of $10^9$ CFU/mL.

In an embodiment of the third aspect of the invention, optionally in combination with any of the embodiments provided above or below, the composition is an OD formulation and comprises a concentration of the strain as defined in the first aspect of the invention in the range from $1.0\times10^5$ to $1.0\times10^{12}$ CFU/mL and also comprises an oily ingredient, in an embodiment is a vegetable oil, in another embodiment is soy oil or soybean oil.

In an embodiment of the third aspect of the invention, optionally in combination with any of the embodiments provided above or below, the composition is an OD formulation and comprises a concentration of the strain as defined in the first aspect of the invention in the range from $1.0\times10^5$ to $1.0\times10^{12}$ CFU/mL and also comprises an oily ingredient, an organic ester and silica. In another embodiment, the oily ingredient is a vegetable oil; in another embodiment is soy oil. In another embodiment is soybean oil a 69%, the organic ester (for example ester of ethoxylated fatty acid) is at 20%, the silica is at 1% and the strain is as TGAI at 10%.

"Agriculturally acceptable compounds" refers to those compounds and/or materials, which are suitable for use in agriculture. In general, said compounds should be non-toxic to humans and preferably should be environment-friendly.

In a particular embodiment of the third aspect of the invention, optionally in combination with any of the embodiments provided above or below, the compositions of the invention may contain compounds for improving the adhesion of the strains in the plants to be treated, as well as phytostrengthener compounds, nutrients, wetting agents, stabilizers, osmotic protectors, antioxidants, sunscreens, buffering compounds or combinations thereof.

Examples of adhesion products we gelatin, starch, pectins, alginates and various types of gums such as xanthan. Many of these compounds are also wetting agents. In the case of sunscreens, Congo red, calcium carbonate and wax emulsions can be used. The phytostrengtheners are compounds that can facilitate male crops develop robustness or tolerance towards pathogens or adverse environmental conditions, for example, jasmonic acid analogues and some plant defense stimulants such as harpins, chitosans, and laminarins. Additionally, examples of osmotic protectors we trehalose, betaines and amino acids. Finally, ascorbic acid and glutathione are included among antioxidants.

The compositions of the third aspect of the invention can be prepared by routine protocols, such as by mixing the different ingredients.

A fourth aspect of the invention refers to a method to obtain a mutant of the strain of CECT9165 of *Bacillus halosaccharovorans*, which maintains the nematicidal and insecticidal effect of CECT9165 comprising the step of subjecting the strain of CECT9165 to a genetic engineering technique.

In an embodiment of the fourth aspect of the invention, optionally in combination with any of the embodiments provided above or below, the genetic engineering technique is mutagenesis, such as random mutagenesis (i.e. using chemical or physical agents), by site-directed mutagenesis, combinatorial mutagenesis or insertional mutagenesis; or a recombinant technique, such as transformation (for example, by electroporation, heat-shock or using divalent cation solutions, such as calcium chloride), transduction or conjugation techniques. In another embodiment of the fourth aspect of the invention, the genetic engineering technique is mutagenesis.

In an embodiment of the fourth aspect of the invention, optionally in combination with any of the embodiments provided above or below, the mutant of the strain has a genomic sequence identity of at least 99.8% (99.8% or 99.9%) with the strain CECT9165 of *Bacillus halosaccharovorans*.

In an embodiment of the fourth aspect of the invention, optionally in combination with any of the embodiments provided above or below, the mutant of the strain CECT9165 of *Bacillus halosaccharovorans*, has an average nucleotide identity (ANI) of at least 99.8% (99.8% or 99.9%) with the strain CECT9165 of *Bacillus halosaccharovorans*.

A fifth aspect of the invention refers to a process for obtaining a viable cell suspension derived from the strain CECT9165 of *B. halosaccharovorans* or a mutant thereof of the first aspect of the invention, the process comprising: (i) inoculating the strain in a culture medium, (ii) subjecting the inoculated culture medium of the step (i) to conditions suitable for growth of the strain, and (iii) optionally subjecting the medium resulting from step (ii) to a concentration step.

The term "derived from the strain CECT9165" means that the suspension is obtained from the strain as defined in the first aspect of the present invention.

The strain of the invention may be inoculated in the culture medium at a final concentration comprised from 5 to 7% v/v. Preferably the inoculated culture is in an exponential growth phase. Suitable culture media for the growth of the strain of the invention are synthetic media, such as LB (lysogenic broth) and PM (saline production medium), or media of plant origin such as molasses (e.g. from sugar cane, beets and others). Suitable conditions for strain's growth are temperatures comprised from 4 to 45° C., pH comprised 6 to 9, and oxygen concentration comprised from 50 to 100%. The growth of the strain of the invention is produced by stirring.

In an embodiment of the fifth aspect of the invention, optionally in combination with any of the embodiments provided above or below, the conditions for the strain's growth are temperatures comprised from 28 to 30° C., pH comprised 7 to 8.5, and oxygen concentration comprised from 85 to 100%.

In another embodiment of the process for obtaining the suspension, cells are separated from the medium to obtain a concentrated suspension. Suitable separation techniques include centrifugation or filtration of the culture. Carrying out the centrifugation of the culture, for example, at a minimum of 5000 rpm, cells are obtained in the pellet, which are resuspended in part of the culture medium or in a suitable buffered medium such that the strain concentration is approximately about $1\times10^5$-$1\times10^{12}$ CFU/mL ($10^5$ cfu/mL, $10^6$ cfu/mL, $10^7$ cfu/mL, $10^8$ cfu/mL, $10^9$ cfu/mL, $10^{10}$ cfu/mL, $10^{11}$ cfu/mL or $10^{12}$ cfu/ml).

Once the suspension is obtained, it may be subjected to a dehydration step. Dehydration can be carried out through a lyophilisation process. Alternatively, the suspension can be dehydrated by fluidised bed drying. Another option is to dehydrate the suspension by spray drying or drying in an oven under vacuum. In this regard, another advantageous feature of the strain of the invention is that it exhibits high resistance t dehydrating processes, which are routine in obtaining microorganisms on an industrial scale. In order to improve cell viability, an inert osmotic protector ingredient can be added to the suspension before carrying out the dehydration process.

In another particular embodiment of the fifth aspect of the invention, the process comprises resuspending the cells resulting from the separation step in a suitable buffer to yield a cell concentrated suspension.

Another aspect of the present invention provides a cell-free extract derived from the strain CECT9165 of *B. halosaccharovorans* or a mutant thereof as defined in the first aspect of the invention, said extract being obtainable by a process comprising: (i) inoculating the strain in a suitable culture medium; (ii) subjecting the inoculated culture medium to suitable growth conditions; (iii) separating the cells from the culture medium of step (ii); (iv) collecting the cell-free extract; and (v) optionally subjecting the cell-free extract to a concentration step.

The cell-free medium obtained by the separation processes described above, could be used and/or included in an appropriated formulation directly or subjected t a concentration step to reach a more suitable composition. Thus, in an embodiment of the fourth aspect of the invention to the step of concentration of the cell-free extract that can be performed by dehydration, filtration, ultra-filtration, centrifugation, ultra-centrifugation, precipitation or chromatography.

A sixth aspect of the invention refers t use of an isolated strain of *Bacillus halosaccharovorans*, which has nematicidal and insecticidal effect, for controlling a nematode and/or an insect infection in a plant.

In an embodiment of the sixth aspect of the invention, it refers to the use of an isolated strain of *Bacillus halosaccharovorans*, which has nematicidal and aphidicidal effect, for controlling a nematode and/or an aphid infection in a plant.

A seventh aspect of the present invention refers t a method for controlling an infection caused by nematodes and/or aphids in a plant comprising applying to a part of a plant or to the substrate used for growing said plant a strain of *Bacillus halosaccharovorans* which has nematicidal and insecticidal effect.

In an embodiment of the seventh aspect of the invention, it refers to a method for controlling an infection caused by nematodes and/or aphids in a plant comprising applying to a part of a plant or to the substrate used for growing said plant a strain of *Bacillus halosaccharovorans* which has nematicidal and aphidicidal effect.

In an embodiment of the sixth and seventh aspects of the invention, optionally in combination with any of the embodiments provided above or below, the isolated strain is the strain CECT9165 of *B. halosaccharovorans* or the mutant thereof as defined in the first aspect of the invention.

The strain of the sixth and seventh aspects of the invention can be used as a bacterial culture or as a composition. Therefore, wherein the strain is the one defined in the first aspect of the invention, the bacteria culture is as the bacteria culture defined in the second aspect of the invention and the composition is the composition defined in the third aspect of the invention.

In an embodiment of the seventh aspect of the invention, optionally in combination with any of the embodiments provided above or below, the strain of *B. halosaccharovorans*, or a mutant thereof as defined in the first aspect of the invention is administered to the plant at a dosage regime of $10^5$ to $10^{12}$ CFU/mL ($10^5$ cfu/mL, $10^6$ cfu/mL, $10^7$ cfu/mL $10^8$ cfu/mL, $10^9$ cfu/mL, $10^{10}$ cfu/mL, $10^{11}$ cfu/mL or $10^{12}$ cfu/mL) per day once during several weeks. In an embodiment of the seventh aspect of the invention, optionally in combination with any of the embodiments provided above or below, the strain of *B. halosaccharovorans*, or a mutant thereof as defined in the first aspect of the invention is administered to the plant at a dosage regime of $10^7$ cfu/mL per day once during several weeks.

The dose may be adapted according to the composition of the third aspect of the invention and the formulation of the composition which is used and also according to the weather conditions, any resistance phenomena or other natural factors, the nature of the treatment or the degree of infestation, and according to the plants or sites to be treated.

In an embodiment of the seventh aspect of the invention, optionally in combination with any of the embodiments provided above or below, the strain, the bacterial culture or the composition is applied to plant nursery boxes, during seed treating, seed dressing, seed disinfection, seedling root dipping treatment, planting pit treatment, plant foot treatment, planting row treatment, surface spraying, soil incorporation, or by application to a water culture medium in hydroponic culture.

In an embodiment of the seventh aspect of the invention, optionally in combination with any of the embodiments provided above or below, the part of the plant treated is the seed. This treatment can be achieved by ordinary methods; for example, a method wherein seeds ae dipped in the composition of the third aspect of the invention.

The treatment of the plant, i.e. root and/or the seeds, allows the nematicidal action of the strain of the invention against root-nematodes.

The term "plant" comprises all plant species cultivated by humans, in particular those intended for food or for animal feed, such as cereals, fodder, vegetable, frit crops, vines, and/or for the supply of wood for all purposes (such as heating, housing construction furniture, and/or ornamentation). Example of plants include cereals (for example, rice, barley, wheat, rye, oat and corn), beans (for example, soybean, azuki bean, broad bean, peas and peanuts), fruit trees/fruits (for example, apples, pears, citruses, grapes, peaches, apricots, cherries, olive, nuts, almonds, bananas, berries and strawberries), vegetables (for example, tomato, cabbage, spinach, broccoli, lettuce, onion, garlic, leek and pepper), root crops (for example, potato, carrot, sweet potato, radish, lotus root and turnip), industrial crops (for example, cotton, hemp, paper mulberry, mitsumata, rape, beet, hop, sugarcane, sugar beet, rubber, coffee, tobacco, tea), pepos (for example, pumpkin, cucumber, watermelon, melon), pasture plants (for example, orchardgrass, sorghum, Thimothy-grass, clover, alfalfa), lawn grasses (for example, mascarene grass, bentgrass), crops for flavorings (for example, lavender, rosemary, thyme, parsley, basilica, mint, coriander, pepper, ginger), and flower plants (for example, chrysanthemum, rose, orchids).

The term "part of a plant" includes any segment of the plant, such as the root, stem, leaves and seeds.

The term "seed" includes what is caged seeds, and also plant bodies for vegetative propagation such as bulbs, tubers and seed potato.

In an embodiment of the sixth or the seventh aspect of the invention, optionally in combination with any of the embodiments provided above or below, the plant is tomato, cucumber or potato plant.

The term "substrate" comprises any support for cultivating a plant, and the material therefor is not particularly limited, as far as the plant can grow therein; for example, nursery mats, water, sand, soil, vermiculite, cotton, paper, diatomaceous earth, agar, gel substances, polymeric substances, rock wool, glass wool, wood chips, barks and pumice.

In an embodiment of the seventh aspect of the invention, optionally in combination with any of the embodiments provided above or below, the method of application is performed in the vicinity of the plant or a nursery bed for raising seedlings.

In an embodiment of the seventh aspect of the invention, optionally in combination with any of the embodiments provided above or below, the method of application is performed directly in the plant.

The examples below demonstrate the use of a strain of *B. halosaccharovorans* as a bio-pesticide, in the control of nematodes and aphid infections.

The insecticidal activity against aphids showed by the *B. halosaccharovorans* strain B410 could be extrapolated to other insects of the hemipteran order.

In an embodiment of the sixth and seventh aspects of the invention, optionally in combination with any of the embodiments provided above or below, the insects are hemipteran insects.

In an embodiment of the sixth and seventh aspects of the invention, optionally in combination with any of the embodiments provided above or below, the insects are hemipteran insects of the Aphididae, Adelgidae, Phylloxeridae and/or Aleyrodidae family.

In an embodiment of the sixth and seventh aspects of the invention, optionally in combination with any of the embodiments provided above or below, the hemipteran insect of the Aleyrodidae family is *Trialeurodes vaporariorum* (whiteflies).

In an embodiment of the sixth and seventh aspects of the invention, optionally in combination with any of the embodiments provided above or below, the insects are of the Aphididae family.

In an embodiment of the sixth and seventh aspects of the invention, optionally in combination with any of the embodiments provided above or below, the use of the sixth aspect and the method of the seventh aspect are for controlling preventing the colonization of pest nematodes and/or aphids or treating infested plants. In particular, the invention relates to uses for controlling those plant pests.

The term "treating" therefore is referred to infested plants. The term control comprises preventing infestations of the plants by said pests, repelling or eliminating said pests.

In an embodiment of the sixth and seventh aspects of the invention, optionally in combination with any of the embodiments provided above or below, the use of the sixth aspect and the method of the seventh aspect are for treating a plant infected by pest nematodes or aphids.

In an embodiment of the sixth and seventh aspects of the invention, optionally in combination with any of the embodiments provided above or below, the nematode is a root-knot nematode or a cyst nematode.

In an embodiment of the sixth and seventh aspects of the invention, optionally in combination with any of the embodiments provided above or below, the nematode is of the genus *Meloidogyne*, such as *Meloidogyne incognita* (southern root-knot nematode), *Meloidogyne javanica* (Javanese root-knot nematode), *Meloidogyne hapla* (northern root-knot nematode), and *Meloidogyne arenaria* (peanut root-knot nematode); nematodes of the genus *Globodera*, such as *Globodera rostochiensis* (golden nematode) and *Globodera pallida* (potato cyst nematode); nematodes of the genus *Ditylelenchus*, such as *Ditylelenchus destructor* (potato rot nematode) and *Ditylenchus dipsaci* (bulb and stem nematode); nematodes of the genus *Pratylenchus*, such as *Pratylenchus penetrans* (cobb root-lesion nematode), *Pratylenchus fallax* (chrysanthemum root-lesion nematode), *Pratylenchus coffeae* (coffee root-lesion nematode), *Pratylenchus loosi* (tea root-lesion nematode), and *Pratylenchus vulnus* (walnut root-lesion nematode); nematodes of the genus *Heterodera*, such as *Heterodera glycines* (soybean cyst nematode) and *Heterodera shachtoii*) (sugar beet cyst nematode); nematodes of the genus *Aphelenchoides*, such as *Aphelenchoides besseyi* (rice white-tip nematode), *Aphelenchoides ritzemabosi* (chrysanthemum foliar nematode), and *Aphelenchoides fragarieae* (strawberry nematode);

nematodes of the genus *Aphelenchus*, such as *Aphelenchus avenae* (mycophagous nematode); nematodes of the genus *Radopholus*, such as *Radopholus similis* (burrowing nematode); nematodes of the genus *Tylenchulus*, such as *Tylenchulus semipenetrans* (citrus nematode); nematodes of the genus *Rotylenchulus*, such as *Rotylenchulus reniformis* (reniform nematode); or nematodes that occur in trees, such as *Bursaphelenchus xylophilus* (pine wood nematode).

In an embodiment of the sixth and seventh aspects of the invention, optionally in combination with any of the embodiments provided above or below, the nematode is selected from the genus *Meloidogyne* and *Globodera*.

In an embodiment of the sixth and seventh aspects of the invention, optionally in combination with any of the embodiments provided above or below, the nematode is selected form the group consisting of *Meloidogyne incognita, Meloidogyne javanica, Globodera rostochiensis* and *Globodera pallida*.

The term "Aphid" refers to the insects of the Aphidoidea superfamiy, Aphidae family.

In an embodiment of the sixth and seventh aspects of the invention, optionally in combination with any of the embodiments provided above or below, the aphid is selected from the group consisting of: *Aphis gossypii* (cotton and melon aphid), *Myzus persicae* (green peach aphid), *Myzus varians* (peach-clematis aphid), *Myzus cerasi* (black cherry aphid), *Brachycaudus persicae* (black peach aphid), *Aphis pomi* (green apple aphid), *Brachycaudus helichrysi* (leaf-curing plum aphid), *Hyalopterus pruni* (mealy plum aphid), *Dysaphis plantaginea* (rosy apple aphid), *Dysaphis pyri*, (pear bedstraw aphid), *Acyrthosiphon pisum* (pea aphid), *Macrosiphvm euphorbiae* (pink and green potato aphid), *Aphis spiraecola* (*A. citricola*) (green citrus aphid), *Aphis fabae* (black bean aphid), *Rhopalosiphum maidis* (corn aphid), *Rhopalosiphum padi* (bird cherry-oat aphid), *Sitobion avenae* (English grain aphid), *Diuraphis noxia* (Russian wheat aphid), *Brevicoryne brassicae* (cabbage aphid), *Eriosoma lanigerum* (woolly apple aphid), *Nasonovia ribisnigri*(lettuce aphid), *Amphorophora idaei* (large raspberry aphid), *Toxoptera aurantii* (black citrus aphid and coffee aphid), *Elatobium abietinum* (green spruce aphid) and *Pemphigus bursarius* (lettuce aphid).

In an embodiment of the sixth and seventh aspects of the invention, optionally in combination with any of the embodiments provided above or below, the aphid is of the genus *Aphis*.

In an embodiment of the sixth and seventh aspects of the invention, optionally in combination with any of the embodiments provided above or below, the aphid is *Aphis gossypii*.

In an embodiment of the sixth and seventh aspects of the invention, optionally in combination with any of the embodiments provided above or below, the nematode is selected from the genus *Meloidogyne* and *Globodera*; and wherein the aphid is of the genus *Aphis*.

In an embodiment of the sixth and seventh aspects of the invention, optionally in combination with any of the embodiments provided above or below, the nematode is selected from the genus *Meloidogyne* and *Globodera*; or alternatively, it is selected from the group consisting of *Meloidogyne incognita, Meloidogyne javanica, Globodera rostochiensis* and *Globodera pallida*; or alternatively the aphid is of the genus *Aphis*; or, alternatively, the aphid is *Aphis gossypii*; or, alternatively, the nematode is selected from the genus *Meloidogyne* and the aphid is of the genus *Aphis*; or, alternatively, the nematode is selected from the genus *Globodera* and the aphid is of the genus *Aphis*; or, alternatively, the nematode is *Meloidogyne incognita* or *Meloidogyne javanica* and the aphid is of the genus *Aphis*; or, alternatively, the nematode is *Globodera rostochiensis* or *Globodera pallida* and the aphid is of the genus *Aphis*; or, alternatively, the nematode is selected from the genus *Meloidogyne* and the aphid is the aphid is *Aphis gossypii*; or, alternatively, the nematode is selected from the genus *Globodera* and the aphid is *Aphis gossypii*; or, alternatively, the nematode is selected from the group consisting of *Meloidogyne incognita, Meloidogyne javanica, Globodera rostiochiensis* and *Globodera pallida*, and the aphid is of the genus *Aphis*; or, alternatively, the nematode is *Meloidogyne incognita* and the aphid is of the genus *Aphis*; or, alternatively, the nematode is *Meloidogyne javanica* and the aphid is of the genus *Aphis*; or, alternatively, the nematode is *Globodera rostochiensis* and the aphid is of the genus *Aphis*; or, alternatively, the nematode is *Globodera pallida* and the aphid is of the genus *Aphis*; or, alternatively, the nematode is selected from the group consisting of *Meloidogyne incognita, Meloidogyne javanica, Globodera rostochiensis* and *Globodera pallida*, and the aphid is *Aphis gossypii*; or, alternatively, the nematode is *Meloidogyne incognita* and the aphid is *Aphis gossypii*: or, alternatively, the nematode is *Meloidogyne javanica* and the aphid is *Aphis gossypii*; or, alternatively, the nematode is *Globodera rostiochiensis* and the aphid is *Aphis gossypii*; or, alternatively, the nematode is *Globodera pallida* and the aphid is *Aphis gossypii*.

In the present invention the term "infection" comprises asymptomatic infection or symptomatic infection of the plant caused by a nematode.

In an embodiment of the sixth and seventh aspects of the invention, optionally in combination with any of the embodiments provided above or below, the control can be performed in any plant.

An eighth aspect of the present invention relates to a kit that comprises an effective amount of the strain, or the mutant thereof as defined in the first aspect of the invention, or the bacterial culture of the second aspect of the invention or the composition of the third aspect of the invention.

All the embodiments provided above for the strain, the bacterial culture and the composition are also embodiments of the kit of the eighth aspect of the invention.

In an embodiment of the eighth aspect of the invention, optionally in combination with any of the embodiments provided above or below, the kit may comprise a weekly, monthly, or other periodic dose of the strain of the first aspect of the invention. As an illustrative example, a kit comprising a weekly dose may comprise seven discrete compositions comprising the strain (seven daily doses). As another example, a kit comprising a monthly dose may comprise thirty compositions comprising the strain of the first aspect of the invention.

In case the strain of the first aspect of the invention is lyophilized, the kit of the eighth aspect of the invention can contain an edible resuspension agent, such as water.

In another embodiment of the eighth aspect of the invention, optionally in combination with any of the embodiments provided above or below, the kit comprises means to facilitate dosing compliance. For example, the kits may be particularly advantageous for the purpose of ensuring that the person who used it is performing the correct administration of the effective amount of the strain of the invention to the plant on the appropriately prescribed schedule. Blister cards or other containing devices appropriately configured may be particularly suitable for clearly illustrating sequence or timing of administration of the various components. The kit may be obtained as one card, or cases of four, six, seven (e.g., a weekly supply), or eight cards co-packaged together. Additionally, monthly or other types of kits may be obtained.

The kit that comprises the isolated strain, or the mutant, of the first aspect of the invention can comprise any means that allows the correct culture of the strain of the invention, such as culture medium, supplements or antibiotics, as well as instructions for the correct preparation and/or application to the plant.

A ninth aspect of the present invention relates to the use of the kit of the eighth aspect of the invention for controlling of a nematode infection and/or an aphid infection in a plant.

All the embodiments provided above under the seventh and eighth aspects of the invention, regarding the particular infections and plants, among others, are also embodiments of the ninth aspect.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples and drawings are provided by way of illustration, and they are not intended to be limiting of the present invention. Reference signs related to drawings and placed in parentheses in a claim, are solely for attempting to increase the intelligibility of the claim, and shall not be construed as limiting the scope of the claim. Furthermore, the present invention covers all possible combinations of particular and preferred embodiments described herein.

EXAMPLES

Example 1. Characterization of the *B. halosaccharovorans* Strain B410

1.1. Example

The strain of the present invention was sequenced and characterized in terms of its temperature range, pH range, and salinity range and biofilm production.

Materials and Methods

The strain B410 of *B. halosaccharovorans* was isolated in an agricultural soil under organic farming regime from Almeria (South of Spain). Identification of the bacterial isolate was achieved using 16S rRNA gene sequence analysis.

Other *Bacillus* isolates were used as comparison, including other strains from the Futureco Bioscience collection and strains purchased from the Deutsche Sammlung von Mikroorganismen und Zellkulturen GmbH (DSMZ) collection. The other strains form the Futureco Bioscience were the following: B2399, *Bacillus litoralis*; B2309, *Bacillus litoralis/niabensis/simplex*; B2525, *Bacillus niabensis*; B145, *Bacillus niabensis*; B149, *Bacillus niabensis/litoralis/Bacillus* sp.; and B1203, *Bacillus niabensis*. The strains from the DSMZ collection were included as a reference and were the following: DSM17723 (*Bacillus niabensis*), DSM 25387 (*Bacillus halosaccharovorans*) and DSM16303 (*Bacillus litoralis*).

Identification of the bacterial isolates was achieved using 16S rRNA gene sequence analysis. Cultures were routinely grown at 28° C. in Marine Broth medium on a rotary shaker at 200 rpm. Template DNA was isolated using the Quick DNA Fungal/Bacterial Kit according to manufacturer's instructions (Zymo Research). The 16S rRNA gene sequencing was performed as described next. A PCR reaction mix, which consisted of 2.5 µL 10×$NH_4$ Buffer (Bioline), 0.75 µL 50 mM $MgCl_2$, 0.625 µL dNTP mix 10 mM 0.5 µL primer 8f 10 µM (SEQ ID NO:1 5'-AGAGTTT-GATCCTGGCTCAG-3'), 0.8 µL primer 1492r 10 µM (SEQ ID NO:2 5'-ACCTTGTTACGACTT-3'), 0.25 µL Biotaq Taq polymerase (5 U/µL; Bioline), 17.875 µL nanopure water and 2 µL template DNA, was amplified according to the following program: 95° C. 5 min; 35 cycles of 95° C. 30 s, 54° C. 30 s and 72° C. 60 s, and 72° C. 5 min. The PCR product was purified using the EZNA Cycle Pure Kit (Omega Bio-Tek) according to manufacturer's instructions. The purified PCR product was sequenced by an external sequencing service (Secugen) using the primer 1492r (SEQ ID NO: 2) and the Sanger method with BigDye® Terminator v3.1 (Applied Biosystems) according to manufacturer's instructions.

To determine the optimum temperature for the growth of selected *Bacillus* isolates, each strain was streaked on the surface of Nutrient agar plates that were then incubated at temperatures of 4° C., 40° C., 42° C., 45° C. and 50° C. Bacterial growth was evaluated every day during 6 days of incubation.

pH range of growth at 28° C. of the strain was determined in sterile 96-well plates. For the experiment, bacteria were first grown overnight in Marine Broth. After that, 100 µL of bacterial suspensions with a final optical density at 600 nm ($OD_{600}$) of 0.01 were added to LB medium at following pHs: 6.48, 7.03, 9.33, 10.04 and 10.98. Then, 200 µL of each *Bacillus* isolate was inoculated for pH (2 wells per pH). The plates were read after 24 h of incubation at 28° C. To determine end points, several approaches were taken into account. Bacteria growth was evaluated by optical density at 620 nm ($OD_{620}$). Cell viability was confirmed by addition of 30 µl of 0.01% resazurin. Any colour changes from blue-purple to pink were recorded as positive.

The effect of salinity on the rate of growth of collection strain at 28° C. was determined in sterile 96-well plates by two-fold serial dilutions of NaCl in 100 µL of LB without NaCl. For the experiment, bacteria were first grown overnight in Marine Broth. After that, 100 µL of bacterial suspensions with a final optical density at 600 nm ($OD_{600}$) of 0.01 were added to the wells containing the following NaCl dilutions: 15, 10, 7.5, 5, 3.75, 2.5, 1.875, 1.25, 0.93, 0.65, 0.465 and 0%. The plates were read after 48 h of incubation at 28° C. To determine MIC end points, several approaches were taken into account. The lowest concentration showing no bacterial growth as evaluated by visual inspection was initially taken as the MIC value, and cell viability was confirmed by addition of 30 µl of 0.01% resazurin. Any color changes from blue-purple to pink were recorded as positive and, in this case, the MIC was defined as the lowest NaCl concentration lacking this colour change. In addition to visual MIC evaluation and before adding resazurin, the $OD_2$ were determined in each well.

Biofilm production at 28° C. of collection strain was determined in sterile 96-well plates by 21 well replicas. For the experiment, bacteria were first grown overnight in Marine Broth. After that, 200 µL of bacterial suspensions with a final optical density at 600 nm ($OD_{600}$) of 0.1 in Marine Broth were added to the wells. The plates were read after 72 h of incubation at 28° C. Biofilm production was reported as Relative Biofilm. After incubation optical density of plates were read at 620 nm, after that biofilm were stained with crystal violet 0.1% and diluted with ethanol in order to obtain its optical density at 620 nm. Relative Biofilm was the relation of OD of biofilm staining with crystal violet at 620 nm divided by OD at 620 nm of initial cell growth.

Results:

The sequencing revealed a sequence (SEQ ID NO: 3) which was 98% identical to that of B. halosaccharovorans strain E33 (NCBI accession number NR_109116.1; database accession date Oct. 1, 2018) (according to Stoddard S F, et al. Nucleic Acids Res. 2015 January; 43:D593-8).

Temperature growth range of all Bacillus isolates resulted to be similar due to most of them grow from 4° C. to 45° C. except DSM 17723, which resulted to be capable of growing at 50° C. All of them were considered mesophyll bacteria.

B410 pH range growth was from 6.48 to 9.33, and, therefore, it was considered neutrophil strain, the same for strains B2525 and DSM 253887. B145, B149, B1203, DSM 17723 grew from 6.48 to 7.03 and these strains were considered neutrophil bacteria too. B2399 and B2309 did not grow in these assay conditions. In this assay, DSM 160303 only grew at 9.33 being considered alkaliphile.

B410 was the only strain tested capable of growing from 0% to 10% of NaCl and it was considered a halotolerant strain. Its optimum salinity range of growing was from 1.25% to 3.75%. B2399, B145, B149, B1203 and DSM 17723 salinity range growth were more limited, as much from 0% to 3.75% being all of them non halotolerant bacteria. It is worth to mention that B145, B149 and DSM 17723 did not grow at 0% of NaCl because they needed some NaCl for growing. B2309, B2525, DSM 25387 and DSM 16303 did not grow in this assay conditions.

B410 was biofilm producer, the same as B2309, B2525, B149, DSM 17723, DSM 25387 and DSM 16303 strains. B2525 and DSM 25387 were very high biofilm producers.

Despite of Bacillus isolates from this study were from close species, every strain evaluated resulted to be different of each other, which explained why they growth conditions were different. Looking at the results globally, on the one hand, we could see that B410, B145, B149, B1203 and DSM 17723 had grown in al assay conditions and, therefore, all parameters of this study for these strains could have been evaluated. However, in the other hand, B2309, B2525, DSM 25387 and DSM 16303 presented growth problems in some assay conditions. Every strain was different from each other because none of any strain global results matched with any other.

B410 was described as mesophyll, neutrophil, halotolerant and biofilm forming strain. The performed assays demonstrated that B410 strain was different from other strains tested because of its high tolerance to NaCl and because it was capable of growing in al assays conditions.

1.2. Example

The strain of the present invention was characterized in terms of its biochemical characteristics.

Materials and Methods

The strains used were Bacillus halosaccharovorans isolate from Futureco Bioscience collection (B410) and the DSM25387 strain form the Deutsche Sammlung von Mikroorganismen und Zellkulturen GmbH (DSMZ) collection, as a reference.

Enzymatic activities were determined using API-50CH® (bioMérieux, Madrid, Spain), following the manufacturer's instructions. Briefly, the bacteria were resuspended in API®-50 CHL medium or API® 50 CHB/E medium. The suspension was used t fill the tubes (cupules) on the API® strips. During incubation of the API® strips, fermentation was revealed by a color change in the tube, caused by the production of acid and detected by the pH indicator present in the medium.

Oxidase activity was measured using Bactident® Oxidase strips (Merk-chemicals) following manufacturer's instructions. Catalase activity was measured following the protocol described in Vashist Hemraj et al. 2013 "A review on commonly used biochemical test for bacteria" Innovare Journal of Life Science 1(1):1-7.

Results:

According to API-50CHI, B410 utilized the following substrates as carbohydrates source: glycerol, L-arabinose, D-xylose, methyl-βD-xylopyranoside, D-galatose, D-glucose, D-fructose, D-mannose, L-rhamnose, inositol, D-mannitol, methyl-αD-mannopyranoside, methyl-αD-glucopyranoside, N-acetylglucosamine, amygdalin, arbutin, esculin, salicin, D-cellobiose, D-maltose, D-lactose, D-melibiose, D-saccharose, D-trehalose, D-melezitose, D-raffinose, starch, glycogen, gentiobiose, D-turanose and D-arabitol. On the other hand, B410 did not utilize erythritol, D-arabinose, D-ribose, L-xylose, D-adonitol, L-sorbose, dulcitol, D-sorbitol, inulin, xylitol, D-lyxose, D-tagatose, D-fucose, L-fucose, L-arabitol, potassium gluconate, potassium 2-ketogluconate and potassium 5-ketogluconate (Table 1b).

B410 and DSM 25387 produced catalase and oxidase. In these tests, only one difference was found between B410 and the type strain DSM 25387, concretely, in methyl-αD-mannopyranoside assimilation.

TABLE 1 (a)

Characterization global results from every Bacillus isolate.

| Strain | Temperature range (° C.) | pH range | Salinity range (%) | Optimum Salinity range (%) | Relative Biofilm |
| --- | --- | --- | --- | --- | --- |
| B410 | 4-45 | 6.48-9.33 | 0-10 | 1.25-3.75 | 0.22 |
| B2399 | 4-45 | No growth | 0-2.5 | 0.65 | 0 |
| B2309 | 4-45 | No growth | No growth | No growth | 0.16 |
| B2525 | 4-45 | 6.48-9.33 | No growth | No growth | 3.08 |
| B145 | 4-45 | 6.48-7.03 | 0.65-1.25 | 0.65 | 0.03 |
| B149 | 4-45 | 6.48-7.03 | 0.65 | 0.65 | 0.25 |
| B1203 | 4-45 | 6.48-7.03 | 0-3.75 | 0-0.47 | 0 |
| DSM 17723 | 4-50 | 6.48-7.03 | 1.25-3.75 | 1.88 | 0.34 |
| DSM 25387 | 4-45 | 6.48-9.33 | No growth | No growth | 1.3 |
| DSM 16303 | 4-45 | 9.33 | No growth | No growth | 0.89 |

TABLE 1b

API-50CH ® results of B410 and DSM 25387.

| Well | Substrate assay for | B410 | DSM 25387 |
|---|---|---|---|
| 0 | Control | Negative | Negative |
| 1 | Glycerol | Positive | Positive |
| 2 | Erythritol | Negative | Negative |
| 3 | D-arabinose | Negative | Negative |
| 4 | L-arabinose | Positive | Positive |
| 5 | D-ribose | Negative | Negative |
| 6 | D-xylose | Positive | Positive |
| 7 | L-xylose | Negative | Negative |
| 8 | D-adonitol | Negative | Negative |
| 9 | Methyl-βD-xylopyranoside | Positive | Positive |
| 10 | D-galatose | Positive | Positive |
| 11 | D-glucose | Positive | Positive |
| 12 | D-fructose | Positive | Positive |
| 13 | D-mannose | Positive | Positive |
| 14 | L-sorbose | Negative | Negative |
| 15 | L-rhamnose | Positive | Positive |
| 16 | Dulcitol | Negative | Negative |
| 17 | Inositol | Positive | Positive |
| 18 | D-mannitol | Positive | Positive |
| 19 | D-sorbitol | Negative | Negative |
| 20 | Methyl-αD-mannopyranoside | Positive | Negative |
| 21 | Methyl-αD-glucopyranoside | Positive | Positive |
| 22 | N-acetylglucosamine | Positive | Positive |
| 23 | Amygdalin | Positive | Positive |
| 24 | Arbutin | Positive | Positive |
| 25 | Esculin, ferric citrate | Positive | Positive |
| 26 | Salicin | Positive | Positive |
| 27 | D-cellobiose | Positive | Positive |
| 28 | D-maltose | Positive | Positive |
| 29 | D-lactose (bovine origin) | Positive | Positive |
| 30 | D-melibiose | Positive | Positive |
| 31 | D-saccharose (sucrose) | Positive | Positive |
| 32 | D-trehalose | Positive | Positive |
| 33 | Inulin | Negative | Negative |
| 34 | D-melezitose | Positive | Positive |
| 35 | D-raffinose | Positive | Positive |
| 36 | Amidon (starch) | Positive | Positive |
| 37 | Glycogen | Positive | Positive |
| 38 | Xylitol | Negative | Negative |
| 39 | Gentiobiose | Positive | Positive |
| 40 | D-Turanose | Positive | Positive |
| 41 | D-lyxose | Negative | Negative |
| 42 | D-tagatose | Negative | Negative |
| 43 | D-fucose | Negative | Negative |
| 44 | L-fucose | Negative | Negative |
| 45 | D-arabitol | Positive | Positive |
| 46 | L-arabitol | Negative | Negative |
| 47 | Potassium gluconate | Negative | Negative |
| 48 | Potassium 2-ketogluconate | Negative | Negative |
| 49 | Potassium 5-ketogluconate | Negative | Negative |

Example 2. In Vitro Nematicidal Activity of *Bacillus halosaccharovorans* Strain B410 Against Eggs of the "Root Knot Nematode"

The in vitro nematicidal activity of *Bacillus halosaccharovorans* strain B410 against eggs of root knot nematode (RKN) *M. javanica* and *M. incognita* eggs was performed and compared with two reference chemicals: Nemacur® (example 2.1.) or Vydate® (example 2.2.).

Materials and Methods

The tests were done in the dark to mimic soil conditions in an incubator (INCUBIG 288L 2000237, JP Selecta, Spain). The incubation temperature was 26° C.

The in vitro nematicidal ability of bacterium *B. halosaccharovorans* strain B410 on a mixture of RKN eggs (*M. javanica* and *M. incognita*) (which was obtained from a tomato plant culture) was evaluated in hatching chambers (Nunclon™ Surface multiwell plates, Nunc, Denmark) in which 2 g of previously sterilized sand was added. The substrate was then inoculated with an aqueous suspension containing 120 eggs of the previously mentioned RKNs (60 eggs of each nematode specie). Immediately after, 200 μl of the biological control agent *B. halosaccharovorans* strain B410 was applied at $7.0 \times 10^8$ CFU/mL in example 2.1 and at $4.5 \times 10^7$ CFU/mL in example 2.2.

A control with a reference chemical at the commercially recommended dose (Nemacur® applied at 0.0125%, active ingredient: Fenamiphos 24%, Bayer in example 2.1. and Vydate® applied at 0.2%, active ingredient: Oxamyl 24%, DuPont in example 2.2.) and a control with sterile distilled water (to establish a reference to compare the results to the normal hatching percentage) were included.

The hatching chamber was incubated at 26° C. for 3 weeks and periodic readings were done at 7, 14 and 21 days after applying the biological control agent to determine the hatching percentage (the counts were performed by means of a Hawksley® chamber; microscope OPTECH BIOSTAR B4, Optech Optical Technology, Germany). Six repetitions of each treatment were performed.

Results:

Example 2.1. Comparison with Fenamiphos

*M. javanica* and *M. incognita* eggs treated with *B. halosaccharovorans* strain B410 showed a significant reduction on egg hatching with respect to the control (FIG. 1).

Three weeks after applying the different treatments, 27.38% of the untreated eggs (control) hatched, whereas 5.68% of those treated with *B. halosaccharovorans* strain B410 hatched and 2.50% of those treated with Nemacur® (reference chemical) hatched. At day 21 after treatment *B. halosaccharovorans* strain B410 reached 79.25% of efficacy in reducing hatching with respect to the control under in vitro conditions. The efficacy in reducing hatching was similar (there were no statistically significant differences) to the reference chemical, which had an efficacy in reducing hatching of 90.86%.

Example 2.2. Comparison with Oxamyl

Figure 2:
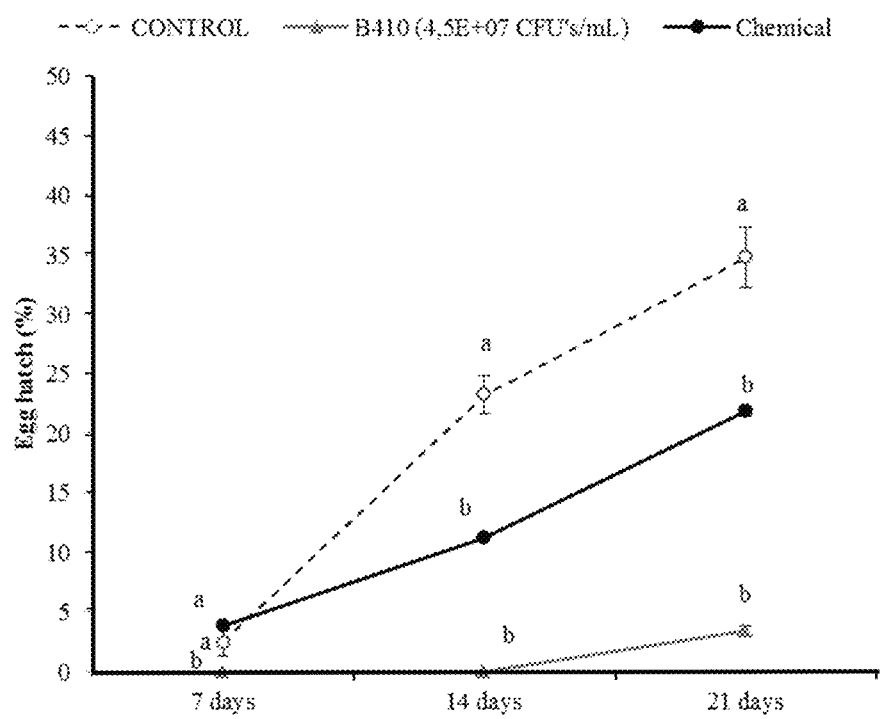
FIG. 2 shows a comparison of the in vitro nematicidal activity of *B. halosaccharovorans* strain B410 and Vydate® ("chemical") against eggs of *M. javanica* and *M. incognita*.

*M. javanica* and *M. incognita* eggs treated with *B. halosaccharovorans* strain B410 showed a significant reduction on hatching with respect to the control (FIG. 2).

Three weeks after applying the different treatments, 34.74% of the untreated eggs (control) hatched, whereas 3.43% of those treated with *B. halosaccharovorans* strain B410 hatched and 21.84% of those treated with Vydate® (reference chemical) hatched. Therefore, *B. halosaccharovorans* strain B410 reached 90.13% of efficacy in reducing hatching with respect to the control under in vitro conditions, whereas in the reference chemical, efficacy in reducing hatching was significantly much lower (37.13%).

Example 3: In Vitro Nematicidal Activity of *Bacillus halosaccharovorans* Strain B410 Against Juveniles (J2) of RKN The in vitro nematicidal ability of bacterium *B. halosaccharovorans* strain B410 was evaluated against a mixture of the RKN *M. javanica* and *M. incognita* juveniles (infective juveniles stage J2).

Materials and Methods:

The tests were done in the dark to mimic soil conditions in an incubator (INCUBIG 288L 2000237, JP Selecta, Spain). The incubation temperature was 26° C. The mixture of RKN *M. javanica* and *M. incognita* juveniles (infective juveniles stage, J2) proceeded form a culture in a tomato plant, and they were placed in hatching chambers (Nunclon™ Surface multiwell plates, Nunc, Denmark), in which 2 g of previously sterilized soil were added.

An aqueous suspension containing a mixture of 200 juvenile forms of *M. javanica*+*M. incognita* (100 nematodes of each specie) was delivered, and then 200 μL of the biological control agent, *B. halosaccharovorans* strain B410 was applied at $4.5 \times 10^7$ CFU/mL. Four repetitions of each treatment were performed.

The hatching chamber was incubated at 26° C. for 14 days and counts were performed by means of the Hawksley® chamber after 7 days and 14 days to determine the number of live juveniles (% survival) (microscope OPTECH BIOSTAR B4, Optech Optical Technology, Germany). A negative control with sterile distilled water and a referenced chemical at a commercial dose (Vydate®) applied at 0.2%, active ingredient: Oxamyl 24%, DuPont) were included.

Figure 3:
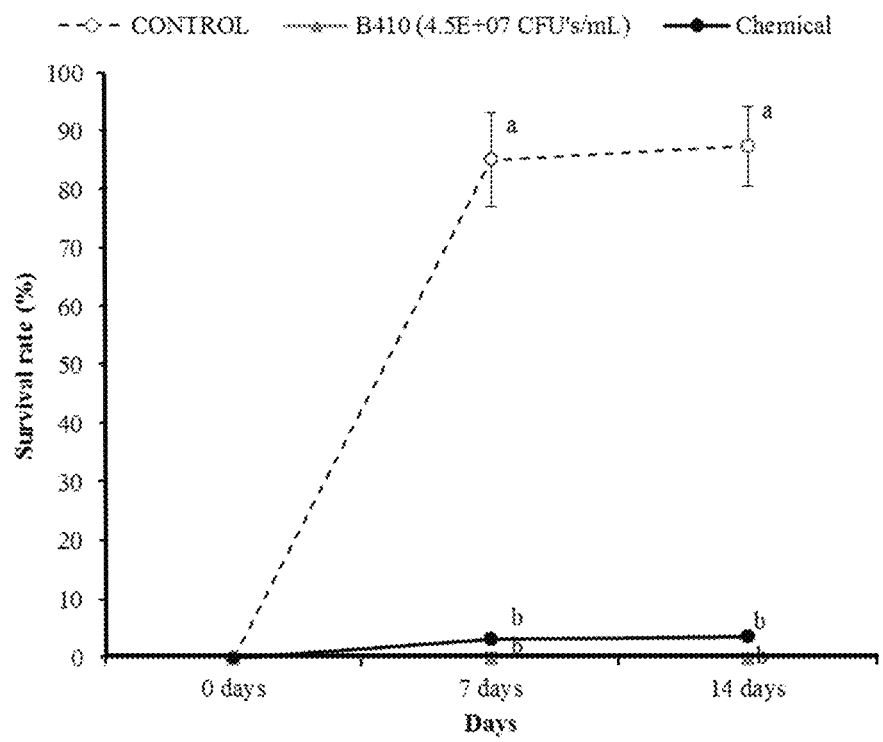
FIG. 3 shows a comparison of the in vitro nematicidal activity of *B. halosaccharovorans* strain B410 and Vydate® ("chemical") against juveniles ($J_2$) of *M. javanica* and *M. incognita*.

Results:

RKN juveniles treated with *B. halosaccharovorans* strain B410 showed a significant reduction on the survival of the juveniles with respect the control when it was applied at $4.5 \times 10^7$ cfu/mL dose (FIG. 3).

Two weeks after applying the different treatments, 87.45% of the juveniles (negative control) survived, whereas 0% of those treated with *B. halosaccharovorans* strain B410 applied at $4.5 \times 10^7$ CFU/mL survived and 3.55% of those treated with the chemical reference survived. Therefore, *B. halosaccharovorans* strain B410 reached 100% of efficacy in reducing the survival of juveniles with respect to the control under in vitro conditions whereas the chemical treatment efficacy was about 97.45%. There were no statistical differences between the efficacy achieved by the microorganism object of the present invention and the chemical reference.

Example 4: In Vitro Nematicidal Activity of *Bacillus halosaccharovorans* Strain B410 Against Eggs of "Potato Cyst Nematodes" *Globodera rostochiensis* and *G. pallida*

The in vitro nematicidal activity of bacterium *B. halosaccharovorans* strain B410 on eggs of Potato Cyst Nematodes (PCNs) *Globodera rostochiensis* and *Globodera pallida* was evaluated.

Materials and Methods

The tests were done in the dark to mimic soil conditions in an incubator (INCUBIG 288L 2000237, JP Selecta, Spain). The incubation temperature was 26° C. Hatching chambers (Nunclon™ Surface multiwell plates, Nunc, Denmark) in which 2 g of previously sterilized sand was added were used.

*Globodera* cysts were obtained from an infested soil using a Fenwick Can (flotation method). Cysts were disinfected with 2% bleach for 2 minutes and rinsed with sterile distilled water. Then cysts were then mechanically crushed in order to release *Globodera* eggs from inside. In example 4.1., the in vitro test consisted of two treatments with 4 repetitions each: 1) Control eggs; 2) Eggs treated with *B. halosaccharovorans* strain B410 (applied at $6.2 \times 10^7$ CFU/mL). In example 4.2. the in vitro test consisted of three treatments with 4 repetitions each: 1) Control eggs; 2) Eggs treated with *B. halosaccharovorans* strain B410 (at $7.0 \times 10^7$ CFU/mL) applied as TGAI and 3) Chemical control (Vydate®, Oxamyl 24%, DuPont), applied at the commercial dose 0.2%.

Three hundred eggs of a mixture of PCNs (150 of *G. pallida* and 150 of *G. rostochiensis* from a population named GGAL-1701 isolated from a potato commercial field in Galicia, Spain) were placed in each well in Example 4.1. On the other hand, in Example 4.2 two hundred and fifty eggs of *G. rostochiensis* (population named GPRA-1803 isolated from a potato commercial field in Catalonia, Spain) were poured in each well. Then, 4.5 mL of 10% Potato Root Diffusate (PRD) solution was added per well in both examples in order to induce eggs to hatch.

To prepare the PRD, Kennebec variety potato sprouts were seeded in trays containing sterile substrate (peat/vermiculite; 1/1, v/v). Sprouted potatoes were left in a climatic chamber for 3 weeks. Then roots of three-week-old plants were submerged in sterile distilled water for 24 hours at 25° C. After 24 hours, the distilled water that had been in contact with the roots was centrifuged (4000 rpm, 15 minutes), filtered (22 μm) and stored in the freezer until needed.

Once the PRD was added, a solution of *B. halosaccharovorans* strain B410 with a concentration of $6.2 \times 10^7$ CFU/mL (example 4.1) or $7.0 \times 10^7$ CFU/mL (example 4.2) was added (200 μL/well). The hatching chambers were maintained at 26° C. throughout the evaluation period. Test readings were taken at 14, 28 and 35 days (using a Hawksley® camber), and 1 mL of new 10% PRD was added every week.

Figure 4:
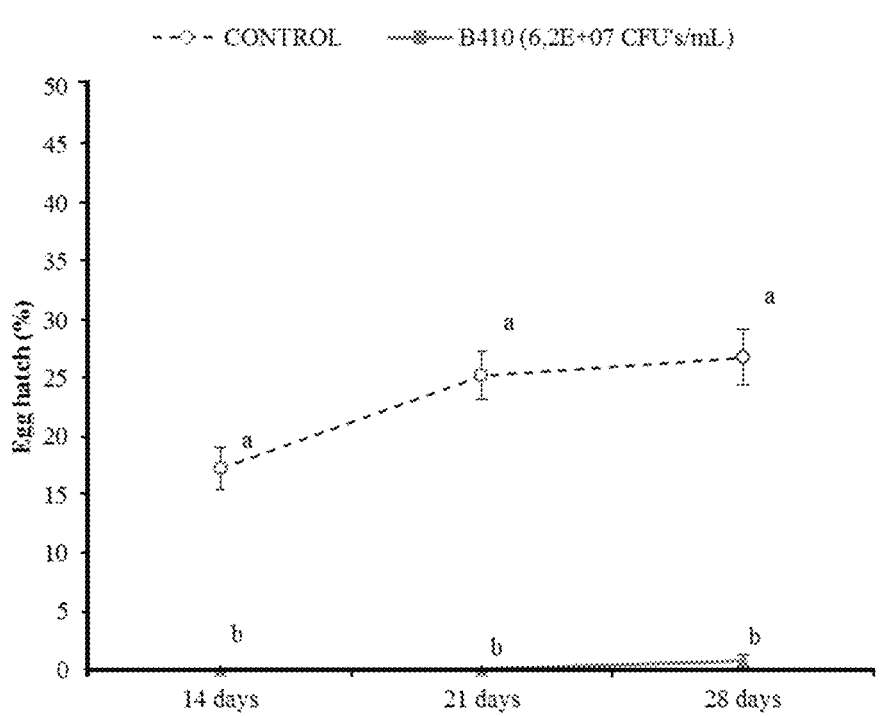
FIG. 4 shows the in vitro nematicidal activity of *B. halosaccharovorans* strain B410 against eggs of *Globodera rostochiensis* and *Globodera pallida*.
Figure 5:
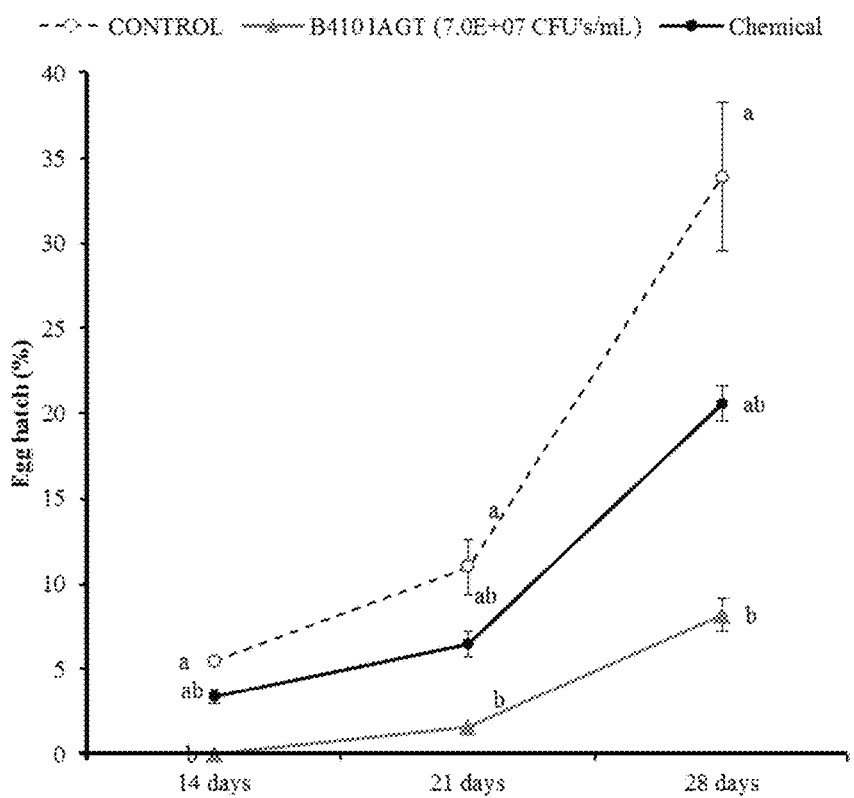
FIG. 5 shows the in vitro nematicidal activity of *B. halosaccharovorans* strain B410 against eggs of *Globodera rostochiensis* compared with the reference chemical (Vydate®)

Results:

Eggs of PCNs treated with *B. halosaccharovorans* strain B410 showed a significant reduction on hatching with respect to the control when it was applied (FIG. 4, example 4.1; and FIG. 5, example 4.2) and with respect to the reference chemical (FIG. 5).

Example 5: In Vivo Nematicidal Activity of *Bacillus halosaccharovorans* Strain B410 Against "Root Knot Nematodes" (*Meloidogyne javanica* and *M. incognita*)

Three examples were performed using the *B. halosaccharovorans* strain B410: as "pellet (example 5.1), as TGAI (example 5.2) and as a formulated prototype (example 5.3). The results for all of them are presented at the end of this section.

Materials and Methods 5.1 In Vivo Nematicidal Activity of a "Pellet" of *B. halosaccharovorans* Strain B410

The in vivo nematicidal ability of bacterium *B. halosaccharovorans* strain B410 was assessed in two experiments in a greenhouse: example 5.1.1 (against *M. javanica*+*M. incognita*) and example 5.1.2 (against *M. javanica*). In both experiments the plants were set up in a greenhouse (temperature 22+2° C., relative humidity RH: 50+10) for 39 days since the first application of the bacterium *B. halosaccharovorans* strain B410.

The experimental design was composed by two different treatments: 1) Control with untreated plants; 2) Plants treated with a suspension of *B. halosaccharovorans* strain B410 applied as a "pellet". Each treatment consisted of 3 replicates with 3 plants per replicate.

The pellet was obtained as follows: 1 mL of a frozen sample of the strain B410 cryovial, (−80° C.) was thawed and grown in Tryptic soy broth (TSB) in a 100 mL flask for 3 days approx. at 30° C. It was centrifuged and that "pellet" that remained (the microorganism as such) was tested in the assay.

Twenty seven tomato seedlings ("Durinta" variety) 3-4 weeks old were transplanted into 3000 cm$^3$ pots filled with a substrate which consisted of a mixture of sand and perlite (3:1; volume:volume). One third of the plants were treated with 10 mL of an aqueous solution containing *B. halosaccharovorans* strain B410 at a dose of 1.04×10$^6$ CFU/mL (example 5.1.1.) or 7.1×10$^7$ CFU/mL (example 5.1.2) three days before transplant (preventive treatment). One day after transplant, all tomato plants were inoculated with a water suspension with root knot nematodes, on example 5.1.1 with *M. javanica*+*M. incognita* (at a dose of 100 infective juveniles per 100 cm$^3$ of substrate, a mixture 50% of each specie obtained from a tomato plant) and in example 5.1.2 with *M. javanica* (at a dose of 100 infective juveniles per 100 cm$^3$ of substrate). Then, 20 mL of an aqueous solution containing *B. halosaccharovorans* strain B410 were applied to the same third of the plants 7 days after inoculation with the nematodes (7 DAI) at a dose of 1.16×10$^8$ CFU/mL (example 5.1.1) or 8.9×10$^5$ CFU/mL (example 5.1.2) and 35 DAI at a dose of 1.89×10$^6$ CFU/mL (example 5.1.1) or 4.1×10$^6$ CFU/mL (example 5.1.2) (see table 2 for a schema of examples 5.1.1 and 5.1.2).

populations were isolated from Almeria, Spain (by IFAPA). There were 3 different sets of plants:

5.2.1 Example

One third of the plants were untreated (control plants without strain B410).

Another one third of the plants were treated once with 10 mL of an aqueous solution containing *B. halosaccharovorans* strain B410 at a dose of 1.30×10$^7$ CFU/mL three days before transplant (preventive treatment). Then, 20 mL of an aqueous solution containing *B. halosaccharovorans* strain B410 were applied to the same third of the plants 7 days after inoculation with the nematodes (7 DAI) at a dose of 4.90× 10$^7$ CFU/mL, 1.57×10$^7$ CFU/mL at 21 DAI and 6.00×10$^7$ CFU/mL at 35 DAI.

And a last third of plants were treated once with 10 mL of an aqueous solution containing *B. halosaccharovorans* strain B410 at a dose of 2.16×10$^6$ CFU/mL three days before transplant (preventive treatment). Then, 20 mL of an aqueous solution containing *B. halosaccharovorans* strain B410 were applied to the same third of the plants 7 days after

TABLE 2

In vivo greenhouse trials against RKN in tomato plants wherein B. halosaccharovorans strain B410 was applied ("pellet")

| | Day 0 1st Application (A, preventive) | Day 3 Transplant | Day 4 Nematode inoculation | Day 11 2$^{nd}$ Application (B, curative) | Day 39 3$^{nd}$ Application (C, curative) |
|---|---|---|---|---|---|
| Example 5.1.1 B410 (CFU/mL) | 1.04 × 10$^6$ | | *M. javanica* + *M. incognita* | 1.16 × 10$^8$ | 1.89 × 10$^6$ |
| Example 5.1.2 B410 (CFU/mL) | 7.1 × 10$^7$ | | *M. javanica* | 8.9 × 10$^5$ | 4.1 × 10$^6$ |

5.2: In Vivo Nematicidal Activity of *Bacillus Halosaccharovorans* Strain B410 TGAI The in vivo nematicidal ability of bacterium *B. halosaccharovorans* strain B410 was assessed in two experiments: example 5.2.1 and example 5.2.2 (as explained below).

The experimental design was composed by three different treatments: 1) Control with untreated plants; 2) Plants treated with a suspension of *B. halosaccharovorans* strain B410 applied as "Technical Grade Active Ingredient" ("TGAI" consisting of 30% of cells and 70% of sucrose) at a dose (in average) about 10$^7$ CFU/mL (TGAI-10$^7$). 3) Plants treated with a suspension of *B. halosaccharovorans* strain B410 applied as a TGAI at a dose (in average) about 10$^6$ CFU/mL (TGAI-10$^6$). Each treatment consisted of 3 replicates with 3 plants per replicate.

Twenty seven tomato seedlings ("Durinta" variety) 3-4 weeks old were transplanted into 3000 cm$^3$ pots filled with a substrate which consisted of a mixture of sand and (3:1; volume-volume). One day after transplant, all tomato plants were inoculated with a water suspension with mixture of root knot nematodes, *M. javanica*+*M. incognita* (at a dose of 100 infective juveniles per 100 cm$^3$ of substrate). It was a mixture of said nematodes, 50% of *M. javanica* (population AL05) plus 50% of *M. incognita* (population AL09); the two inoculation with the nematodes (7 DAI) at a dose of 4.40× 10$^7$ CFU/mL, 1.75×10$^6$ CFU/mL at 21 DAI and 4.30×10$^6$ CFU/mL at 35 DAI.

5.2.2 Example

One third of the plants were untreated (control plants without strain B410).

Another one third of the plants were treated once with 10 mL of an aqueous solution containing *B. halosaccharovorans* strain B410 at a dose of 1.36×10$^8$ CFU/mL three days before transplant (preventive treatment). Then, 20 mL of an aqueous solution containing *B. halosaccharovorans* strain B410 were applied to the same third of the plants 7 days after inoculation with the nematodes (7 DAI) at a dose of 3.36× 10$^7$ CFU/mL, 5.40×10$^7$ CFU/mL at 21 DAI and 6.60×10$^7$ CFU/mL at 35 DAI.

And a last third of plants were treated once with 10 mL of an aqueous solution containing *B. halosaccharovorans* strain B410 at a dose of 1.76×10$^7$ CFU/mL three days before transplant (preventive treatment). Then, 20 mL of an aqueous solution containing *B. halosaccharovorans* strain B410 were applied to the third of the plants 7 days after inoculation with the nematodes (7 DAI) at a dose of 2.60×10$^6$ CFU/mL, 4.10×10$^6$ CFU/mL at 21 DAI and 7.60×10$^6$ CFU/mL at 35 DAI.

TABLE 3

Schema of the treatments performed using *B. halosaccharovorans* strain B410 application plant in in vivo greenhouse trials against Root Knot Nematodes (RKNs) in tomato plants

| | Day 0<br>$1^{st}$<br>application<br>(A,<br>preventive) | Day 3<br>transplant | Day 4<br>nematode<br>inoculation | Day 11<br>$2^{nd}$<br>application<br>(B,<br>curative) | Day 25<br>$3^{nd}$<br>application<br>(C,<br>curative) | Day 39<br>$4^{th}$<br>application<br>(D,<br>curative) |
|---|---|---|---|---|---|---|
| Experiment 5.2.1. | $1.30 \times 10^7$ | | *M. javanica* + *M. incognita* | $4.90 \times 10^7$ | $1.57 \times 10^7$ | $6.00 \times 10^7$ |
| | $2.16 \times 10^6$ | | *M. javanica* + *M. incognita* | $4.40 \times 10^6$ | $1.75 \times 10^6$ | $4.30 \times 10^6$ |
| Experiment 5.2.2. | $1.36 \times 10^8$ | | *M. javanica* + *M. incognita* | $3.36 \times 10^7$ | $5.40 \times 10^7$ | $6.60 \times 10^7$ |
| | $1.76 \times 10^7$ | | *M. javanica* + *M. incognita* | $2.60 \times 10^6$ | $4.10 \times 10^6$ | $7.60 \times 10^6$ |

5.3: In Vivo Nematicidal Activity of *Bacillus halosaccharovorans* Strain B410 "Formulated Prototypes"

The in vivo nematicidal ability of a nematicidal formulation based on the bacterium *B. halosaccharovorans* strain B410 was assessed in two experiments, example 5.3.1 and example 5.3.2 both against a mixture of *M. javanica* and *M. incognita* (obtained from a tomato plant).

Materials and Methods

The experimental design was composed by two different treatments: 1) Control with untreated plants; 2) Plants treated with a suspension of *B. halosaccharovorans* strain B410 applied as a "formulation" (OD) at a dose (in average) $3.36 \times 10^7$ cfu/mL (Formulation-$10^7$) in example 5.3.1 or $2.61 \times 10^7$ cfu/mL (Formulation-$10^7$) in example 5.3.2. Both treatments consisted of 3 replicates with 3 plants per replicate Eighteen tomato seedlings ("Durinta" variety) 3-4 weeks old were transplanted into 3000 cm³ pots filled with a substrate which consisted of a mixture of sand and perlite (3:1; volume:volume). One day after transplant, all tomato plants were inoculated with a water suspension with root knot nematodes, *M. javanica*+*M. incognita* (at a dose of approximately 100 infective juveniles per 100 cm³ of substrate) in example 5.3.1 or *M. javanica* (at a dose of approximately 100 infective juveniles per 100 cm³ of substrate) in example 5.3.2. There were two different sets of plants:

Half of the plants were untreated (control plants). The other half of the plants was treated once with 20 mL of an aqueous solution containing 1% of a formulation based on *B. halosaccharovorans* strain B410 at a dose of $2.92 \times 10^7$ CFU/mL (example 5.3.1) or $2.64 \times 10^7$ (example 5.3.2) at the day of transplant (preventive treatment). Then, 20 mL of an aqueous solution containing 1% of the formulation based on *B. halosaccharovorans* strain B410 were applied to the same half of the plants 7 days after inoculation with the nematodes (7 DAI) at a dose of $3.60 \times 10^7$ CFU/mL (example 5.3.1) or $4.20 \times 10^7$ (example 5.3.2); $3.30 \times 10^7$ CFU/mL (example 5.3.1) or $1.80 \times 10^7$ CFU/mL (example 5.3.2) at 21 DAI; and $3.60 \times 10^7$ CFU/mL (example 5.3.1) or $1.80 \times 10^7$ CFU/mL (example 5.3.2) at 35 DAI. See table 4 for a schema of examples 5.3.1 and 5.3.2.

The formulation consisted of mixture of: soy vegetable oil (Gustave Hess, Germany) 690 g/L+Silica (Silysiamont, Italy) (10 g/L)+Ester of ethoxylated fatty acid (Lamberti-Chemical Specialist, Italy) (200 g/L)+TGAI (strain of the invention) (100 g/L). The materials were mixed in a laboratory reactor using a high speed stirrer designed for oils.

TABLE 4

Formulation based on *B. halosaccharovorans* strain B410 application plant in an in vivo greenhouse trial against RKN in tomato plants

| | Day 1<br>Transplant +<br>1st Application<br>(A, preventive) | Day 2<br>Nematode<br>inoculation | Day 9<br>$2^{nd}$<br>Application<br>(B, curative) | Day 23<br>$3^{nd}$<br>Application<br>(C, curative) | Day 37<br>$4^{th}$<br>Application<br>(D, curative) |
|---|---|---|---|---|---|
| Example 5.3.1 | $2.92 \times 10^7$ | *M. javanica* + *M. incognita* | $3.60 \times 10^7$ | $3.30 \times 10^7$ | $3.60 \times 10^7$ |
| Example 5.3.2 | $2.64 \times 10^7$ | *M. javanica* | $4.20 \times 10^7$ | $1.80 \times 10^7$ | $1.80 \times 10^7$ |

In all cases, the plants were set up in a greenhouse; in example 5.1: temperature (T): 22±2° C.—Relative humidity (HR): 50±10 for 10 weeks since the seedlings were transplanted; in examples 5.2 and 5.3. T: 25±2-HR: 50±10) for 9 weeks since the seedlings were transplanted.

For all experiments (experiments 5.1, 5.2 and 5.3), at the end of the bioassay the total number of eggs per plant and eggs per gram of root were determined in each treatment they were extracted from the radicular system by mechanical disruption and passed through different sieves from 200 mesh (75 μm) to 500 mesh (25 μm) (the counts were performed by means of a Hawksley® chamber; microscope Optech biostar B4, Optech Optical Technology, Germany).

Pf in means of number of eggs/plant and nematode Reproduction (eggs/gram of fresh root) was assessed in al treatments 10 or 9 weeks after transplant (10 weeks in the case of the"pellet" and 9 weeks in the case of the TGA and OD formulation).

In all cases ater the treatments performed, data were subjected to analysis of variance (ANOVA) using R software (R Core Team, 2013, Austria). The significant differences among treatments were determined by the Least Significant Difference (LSD) test at P≤0.05.

Results of the In Vivo Experiments Using Pellet, TGAI and OD Formulation:

The results obtained in the in vivo assays showed that the *B. halosaccharovorans* strain B410 applied as a pellet, as a TGAI or at a 1% OD formulation had nematicidal activity against RKN, they showed a significant reduction on both parameters with respect to the control in all cases (see table 5 below).

TABLE 5

Efficacy (%) of *B. halosaccharovorans* strain B410 TGAI against RKN in tomato plants in greenhouse corrected with respect to the control used as a reference.

| Examples and treatments | Efficacy (%) on Final Population ($P_f$)(eggs/plant) | Efficacy (%) on Reproduction (eggs/g fresh root) |
|---|---|---|
| 5.1.1; pellet | 57.32 | 76.21 |
| 5.1.2; pellet | 58.11 | 60.69 |
| 5.2.1; strain B410 TGAI $10^7$ | 76.95 | 61.58 |
| 5.2.1; strain B410 TGAI $10^6$ | 34.24 | 29.42 |
| 5.2.2; strain B410 -TGAI $10^7$ | 56.01 | 51.64 |
| 5.2.2; strain B410 -TGAI $10^6$ | 35.10 | 32.01 |
| 5.3.1; strain B410 - OD Formulation $10^7$ | 46.42 | 41.77 |
| 5.3.2; strain B410-OD Formulation $10^7$ | 54.89 | 48.83 |

In the case of the TGAI, the % of efficacy was significantly higher (on Final Population and on Reproduction) in the plants treated with *B. halosaccharovorans* strain B410-TGAI 10 compared with the plants treated with a lower dose (*B. halosaccharovorans* strain B410-TGAI $10^6$).

Example 6: Laboratory Study of the Insecticide Efficacy of *Bacillus halosaccharovorans* Strain B410 Against Aphids To determine the insecticidal efficacy of *B. halosaccharovorans* strain B410 against Cotton Melon aphids (*Aphis gossypii*) a laboratory study was performed.

Materials and Methods:

The experiment was performed in the testing facility of i2LResearch Ltd. (Newcastle, UK) under controlled laboratory conditions.

The insecticidal activity of the *B. halosaccharovorans* strain B410 was compared to the same activity in other bacterial strains from Futureco Bioscience Microorganisms Collection. Those microorganisms were the following: B1325 (*Bacillus safensis*), B788 (*Caulobacter* sp/*Caulobacter segnis*), B96 (*Lysinibacillus sphaericus/Lysinibacillus fusiformis*) and B1001 (*Bacillus humi*) which were selected by its potential insecticidal effect. The four microorganisms (TGAIs) were tested at a standard rate (5E+07 CFUs/mL, application volume of 2 mL). The products tested were diluted in water prior to test initiation and the solution thoroughly agitated to ensure their homogeneity. A negative (water only) control was also included for comparative purposes. Treatments were applied directly onto the insects on plant material at the rates specified by the table below. Each treatment comprised of 3 replicates.

The insects (Cotton, Melon aphids, *Aphis gossypii*) were sourced from an in-house laboratory culture. Mixed sex and aged adults were used in the experiments.

Petri dishes were lined with a leaf disc/fragment, cut from lettuce (*Lactuca sativa*), and mounted on a damp cotton wool pad. Ten aphids were counted into each Petri dish (and placed directly onto plant material). The plant material and aphids were then sprayed with the treatments. Treatments were applied using a small atomiser. All spray equipment was fully calibrated prior to use.

Aphids were assessed at 48, 96 and 144 hours post treatment. At each observation period, insects were scored according to the following criteria:

1. Unaffected/healthy—Individual completed unaffected and exhibiting normal behaviour.
2. Knockdown—Individual is unable to engage in directional movement and/or fly but appendages are vigorously moving with or without probing.
3. Dead—No response to tactile stimuli.

The conditions at treatment application were: temperature, 15.0° C.; humidity (%), non-applicable; and leaf moisture, dry.

All statistical analyses were performed using Minitab (version 16). Data from each assessment were subjected to an Analysis of Variance with treatment as a factor. Tukey HSD comparison tests were subsequently used to distinguish between means. Prior to analysis data were checked to ensure that the assumptions of the statistical model held. Where data were not normally distributed, the ANOVA was performed on the transformed data set.

In all analyses, the probability of no significant differences occurring between treatments was calculated as the F probability value (p (F)). All tests were undertaken at the 95% confidence interval.

Figure 6:
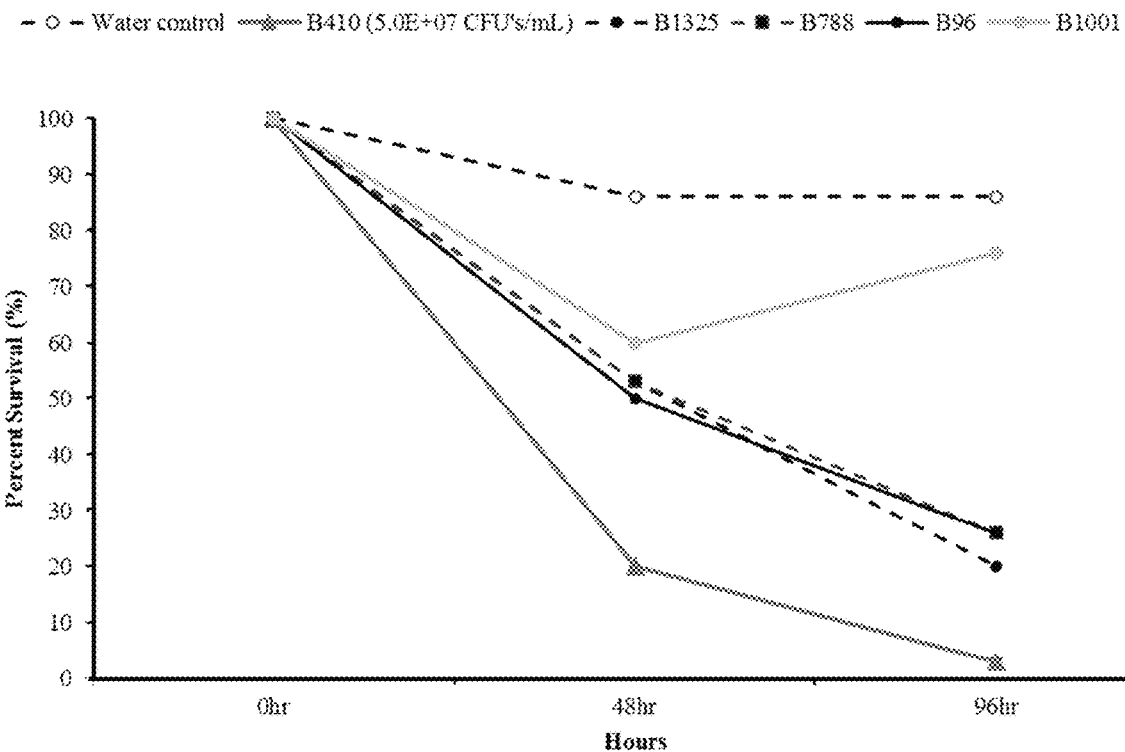
FIG. 6 shows the percentage of aphid survival recorded in lab conditions comparing the treatment with other bacterial strains.
Figure 7:
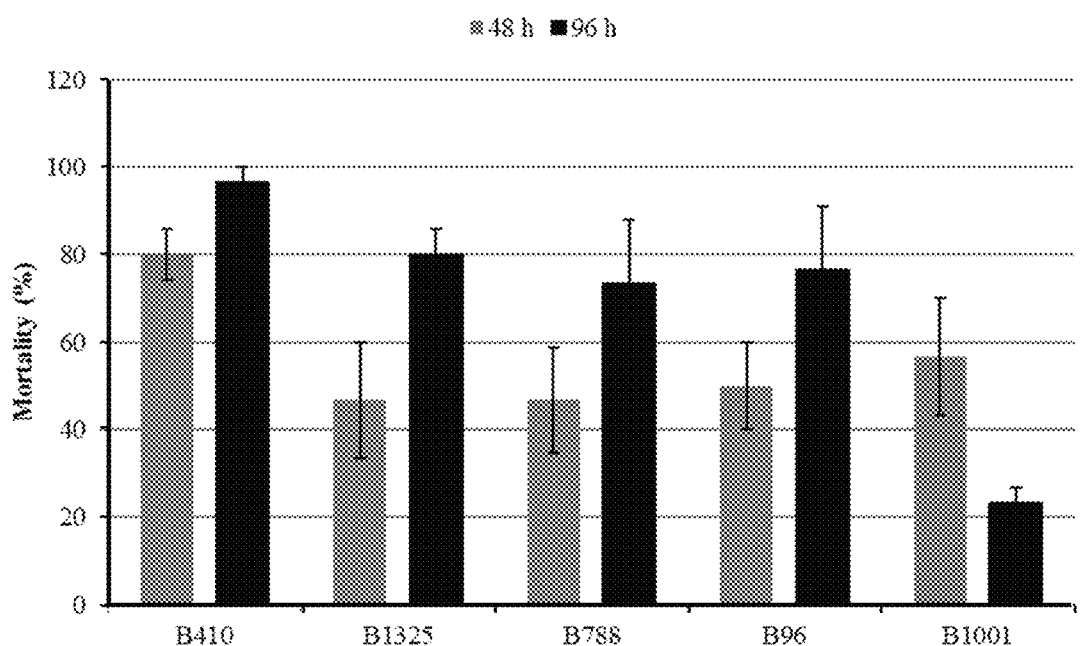
FIG. 7 shows percentage of efficacy of B410 on controlling aphids 48 h and 96 h after treatment under lab conditions compared with the efficacy of other bacterial strains.

Results:

B410 was the fastest acting TGA, affording significant aphid mortality 48 hours after exposure. Results from the ANOVA showed that 48 hours following exposure to test products, B410 was the only treatment to afford significant mortality when compared to the water control. After 96 hours exposure, all products provided significant aphid mortality when compared to the water control (see FIGS. 6 and 7). This trend was continued to the final assessment at 144 hours.

No phytotoxic effects were recorded throughout the duration of the trial.

Example 7: Evaluation of Acute Oral Toxicity of *Bacillus halosaccharovorans* in Mice Materials and Methods:

To determine whether the strain *B. halosaccharovorans* B410 was safe, its oral toxicity in mice was tested.

Materials and Methods:

Three male and three female Balb/C mice of 4-5 weeks old (QC'd albino pathogen free mice; Envigo) were used. Animals fasted overnight before dosing. The day before the experiment, the body weight of the animals was recorded and feces samples were collected from individual animals. Each animal received one oral singe dose of the *B. halosaccharovorans* B410 strain: 100 CFU B410 TGAI (vehicle 200 µl of sterile H$_2$O) (prepared as described previously). Mice received sterile water (vehicle control) were also maintained throughout the study. Mice were housed under controlled environment and monitored for 21 days and the observations were recorded. Daily, once, the following was observed for each animal: skin and fur, eyes and mucous membranes, respiratory system, circulatory system, autonomic and central nervous system, somatomotor activity, behavior pattern, observation of tremors, convulsions, diarrhea, lethargy, salivation, and coma if any. Weights of individual animals checked prior and post gavage once per week. Necropsy was performed at the end of 21 day post oral gavage for assessment of presence or absence of the bacterial strain in the tissues. Tissue collection and blood culture was done aseptically to avoid any cross contamination.

Necropsy: the kidney, brain, liver, lung, spleen, blood and gut lymph node was collected from each animal and immediately kept in dry ice and stored at −20° C. until further processing. RNA was extracted from the above tissues and RT-PCR was performed to determine presence of B410 TGA using the specific primers: "B neoben F1, F1" 5'-CGGAATCGCTAGTAATCGCG-3' (SEQ ID NO: 4); "B neoben R1", 5'-CCCAATCATCTGTCCCACCT-3' (SEQ ID NO: 5); "B neoben F2", 5'-TCGGGTCGTAAAGCTCTGTT-3' (SEQ ID NO: 6); and "B neoben R2", 5'-TTCTGCACTCAAGTTCCCCA-(SEQ ID NO: 7). These two pair of primers were used in order to ensure that the amplification product was the 16S of *B. halosaccharovorans*.

Blood Processing: at necropsy, aseptic whole blood samples were collected from each animal. Immediately following collection, 100 µl of each blood sample was placed and spread on agar plate and maintained at 28° C. for 120 hours. The plates were analyzed at regular intervals for assessment of any bacterial growth.

Clearance of the Microbial Pest Control Agent (MPCA): feces collection on dosing and on day 7, 14 and 21 days were kept at 4° C. for further RNA extraction and RT-PCR analysis.

Blood/Bacterial culture media Meat extract 1 g, Yeast Extract 2 g, Peptone 5 g, NaCl 5 g and Agar 15 g were added (for 1000 ml) and sterilized for 121° C. for 20 min and thereafter was poured into plates and used for the blood culture and B410 TGAI CFU/g determination. RNA extraction protocol: 50 mg of tissue was used for RNA extraction following manufacturer's instructions (RNA Isolation kit Zymo Research, Cat No R1050).

Spike control: 100 µl of 10$^9$ CFU of TGAI was spiked with 50 mg of brain and liver tissue and total RNA was extracted by using the Quick RNA total RNA extraction kit according to manufacturer's instructions (Zymo Research) with addition of Proteinase K and Lysozyme digestion step—included in the aforementioned kit—for isolating total RNA including bacterial RNA.

Positive control: 0.2 g of B410 TGAI diluted serially for 7 times in sterile water and plated (100 µl) and re-confirmed the CFU/g sample. The bacterial colonies grown on agar plates were collected and directly used for total RNA extraction and as a positive control for the study.

cDNA synthesis: Total RNA from tissues and feces were measured in a micro plate reader (Biotek). 2 µg of total RNA (1 µg in case of feces samples) was used for cDNA synthesis by using Superscript IV 1st strand synthesis kit (Life technologies, Cat No: 18091050). Appropriate positive (B410 TGAI) and negative controls (H$_2$O) were also maintained.

RT-PCR assay: 20 µl total of the cDNA mixture was diluted 1:10 fold (tissue samples) and 1:5 fold (feces samples cDNA) and RT-PCR was performed using PowerUp SYBR™ Green Master Mix according to manufacturer's instructions (Life Technologies, Cat No A25776) with an Applied Biosystems StepOne™ real time PCR device. PCR reactions consisted of 5 µL PowerUp™ SYBR™ Green Master Mix, 0.5 µL each specific primer (F1 and R1, or F2 and R2), and 10 ng cDNA as template, in a total reaction volume of 20 µL. The thermal cycling conditions were as follows: 2 min at 50° C., 2 min at 95° C., and 40 cycles of 15 s at 95° C., 15 s at 60° C., and 1 min at 72° C.

Results:

Body weight from the control and *B. halosaccharovorans* B410 gavaged animal were not significantly different. Blood culture plates incubated for 120 h at 28 degree had no visible growth and was concluded negative. Clinical symptoms monitored did not reveal adverse changes. RT-PCR data revealed that the 16srDNA specific primers were not amplified in any of the tissue or feces samples from *B. halosaccharovorans* B410 gavaged animals (Average Ct values 33). The *B. halosaccharovorans* B410 TGAI spiked tissue samples were amplified using the *B. halosaccharovorans* specific primers along with the positive control (average spiked Ct value 20 for brain and 25 for liver). Negative controls (water gavaged) had no amplification in RT-PCR (Average Ct value 32). Positive control 16s rDNA primer amplified at cycle 6 (Ct value 12). The data reveal absence of *B. halosaccharovorans* B410 in any of the samples screened using the specific RT-PCR primers.

Animals had no visible clinical adverse effects and no infectivity or pathogenicity was found. Strain gavaged animals had no visible clinical adverse effects and the bacterial strain was not detected in the blood, feces or other organs examined.

REFERENCES CITED IN THE APPLICATION

WO9404684

Xiang N at a. "Biological control of *Meloidogyne incognita* by Spore-forming Plant Growth-promoting Rhizobacteria on Cotton" Plant Disease 2017(101):774-784.

Sambrook, J. and Russell, D. W. "Molecular Cloning: A Laboratory Manual", Chapter 13, "Mutagenesis", Cold Spring Harbor, 3rd Ed, 2001.

Stoddard S F, at al. rrnDB: improved tools for interpreting rRNA gene abundance in bacteria and archaea and a new foundation for future development. Nucleic Acids Res. 2015 January; 43(Database issue):D593-8

Vashist Hemraj at al. 2013 "A review on commonly used biochemical test for bacteria" Innovare Journal of Life Science 1(1):1-7

Altschul et al., "Basic local alignment search tool", 1990, J. Mol. Biol., v. 215, pages 403-410.

Higgins at al., "CLUSTAL V: improved software for multiple sequence alignment", 1992, CABIOS, 8(2), pages 189-191

Richter M, at al. 2015 JSpeciesWS: a web server for prokaryotic species circumscription based on pairwise genome comparison. Bioinformatics. 2015 Nov. 16. pii: btv681

Aubert at al., "A Markerless Deletion Method for Genetic Manipulation of *Burkholderia cenocepacia* and Other Multidrug-Resistant Gram-Negative Bacteria" Methods Mol Biol 2014; 1197:311-27.

For reasons of completeness, various aspects of the invention are set out in the following numbered clauses:

Clause 1. A strain of *Bacillus halosaccharovorans* deposited at the "Colección Española de Cultivos Tipo" (CECT) under the accession number CECT9165, or a mutant thereof, wherein said mutant is obtained using the CECT9165 of *Bacillus halosaccharovorans* as starting material and maintains the nematicidal effect and aphidicidal effect of CECT9165.

Clause 2. A bacterial culture comprising the strain or the mutant thereof of clause 1, preferably the bacterial culture is an inoculation product.

Clause 3. A composition comprising an effective amount of the strain CECT9165 of *Bacillus halosaccharovorans* of clause 1 or the bacterial culture according of clause 2, and one or more agriculturally acceptable compounds.

Clause 4. The composition of clause 3 wherein the strain is present at a concentration from $10^5$ CFU/ml to $10^{12}$ CFU/ml.

Clause 5. The composition of clauses 3 or 4 wherein the composition is formulated as an oil dispersion formulation, preferably comprising an oily ingredient, an organic ester and silica.

Clause 6. The composition of any one of clauses 3 to 5 which comprises at least one additional pesticide.

Clause 7. A method to obtain a mutant of the strain of CECT9165 of *B. halosaccharovorans* which maintains the nematicidal and insecticidal effect of CECT9165, comprising the step of subjecting the strain CECT9165 to a DNA recombinant technique, preferably mutagenesis.

Clause 8. A process for obtaining a viable cell suspension derived from the strain CECT9165 of *Bacillus halosaccharovorans* or a mutant thereof as defined in clause 1, the process comprising: (i) inoculating the strain in a culture medium, (ii) subjecting the inoculated culture medium of the step (i) to conditions suitable for growth of the strain, and (iii) optionally subjecting the medium resulting from step (ii) to a concentration step.

Clause 9. Use of an isolated strain of *Bacillus halosaccharovorans*, which has nematicidal and insecticidal effect, for controlling of a nematode and/or an aphid infection in a plant.

Clause 10. A method for controlling an infection caused by nematodes and/or aphids in a plant comprising applying to a part of a plant or to the substrate used for growing said plant an isolated strain of *Bacillus halosaccharovorans* which has nematicidal and insecticidal effect.

Clause 11. The use of clause 9 or the method of clause 10, wherein the isolated strain is applied in the form of a bacterial culture or in the form of a composition, the composition further comprising one or more agriculturally acceptable compounds.

Clause 12. The use of any one of clauses 9 or 11 or the method of any one of clauses 10 or 11, wherein: the nematode is selected from the genus *Meloidogyne* and *Globodera*; or alternatively, it is selected from the group consisting of *Meloidogyne incognita, Meloidogyne javanica, Globodera rostochiensis* and *Globodera pallida*; or alternatively the aphid is of the genus *Aphis*; or, alternatively, the aphid is *Aphis gossypi*; or, alternatively, the nematode is selected from the genus *Meloidogyne* and the aphid is of the genus *Aphis*; or, alternatively, the nematode is selected from the genus *Globodera* and the aphid is of the genus *Aphis*; or, alternatively, the nematode is selected from the genus *Meloidogyne* and the aphid is *Aphis gossypii*; or, alternatively, the nematode is selected from the genus *Globodera* and the aphid is *Aphis gossypii*; or, alternatively, the nematode is selected from the group consisting of *Meloidogyne incognita, Meloidogyne javanica, Globodera rostochiensis* and *Globodera pallida*, and the aphid is of the genus *Aphis*; or, alternatively, the nematode is selected from the group consisting of *Meloidogyne incognita, Meloidogyne javanica, Globodera rostochiensis* and *Globodera pallida*, and the aphid is *Aphis gossypii*.

Clause 13. The use of any one of clauses 9, 11 or 12, or the method of any one of the clauses 10, 11 or 12, wherein the isolated strain is the one as defined in claim 1.

Clause 14. A kit comprising an effective amount of the strain of clause 1, the bacterial culture of clause 2 or the composition as defined in any one of the clauses 3-6.

Clause 15. Use of the kit of clause 14 for controlling an infection caused by nematodes and/or aphids in a plant.

The invention claimed is:

1. A pesticide composition comprising:
a *Bacillus halosaccharovorans* strain deposited at the "Colección Española de Cultivos Tipo" (CECT) under the accession number CECT9165, or a mutant thereof having an average nucleotide identity of at least 99.8% with the strain deposited under the accession number CECT9165; and
a vegetable oil, a soy oil, a soybean oil, or a mixture of a vegetable oil and a soy oil,
wherein said mutant is obtained using the CECT9165 of *Bacillus halosaccharovorans* as starting material and maintains the nematicidal effect and aphidicidal effect of CECT9165.

2. The pesticide composition according to claim 1, comprising an inoculation product comprising the strain CECT9165 or the mutant thereof.

3. The pesticide composition according to claim 1, further comprising one or more agriculturally acceptable compounds.

4. The pesticide composition according to claim 1, wherein the strain is present at a concentration from $10^7$ CFU/ml to $10^{12}$ CFU/ml.

5. The pesticide composition according to claim 3, further comprising at least one additional pesticide.

6. The pesticide composition according to claim 3, wherein the strain or the mutant thereof is present at a concentration from $10^7$ CFU/ml to $10^{12}$ CFU/ml and the pesticide composition is formulated as an oil dispersion formulation, optionally further comprising an organic ester, and silica; and optionally, further comprising at least one additional pesticide.

7. The pesticide composition according to claim 3, wherein the strain or mutant thereof is formulated as a pellet.

8. The pesticide composition according to claim 4, formulated as an oil dispersion formulation, and optionally comprising an organic ester, and silica.

9. A pesticide composition comprising:
a *Bacillus halosaccharovorans* strain deposited at the "Colección Española de Cultivos Tipo" (CECT) under the accession number CECT9165; and
a vegetable oil, a soy oil, a soybean oil, or a mixture of a vegetable oil and a soy oil,
wherein the *Bacillus halosaccharovorans* strain is present at a concentration from $10^7$ CFU/ml to $10^{12}$ CFU/ml.

10. A method for controlling an infection caused by a nematode and/or an aphid in a plant, comprising applying to a part of the plant or to a substrate used for growing the plant, the pesticide composition of claim 1.

11. The method according to claim 10, wherein: the nematode is selected from the genus *Meloidogyne* and *Globodera*; or alternatively, the nematode is selected from the group consisting of *Meloidogyne incognita, Meloidogyne javanica, Globodera rostochiensis* and *Globodera pallida*; or alternatively the aphid is of the genus *Aphis*; or, alternatively, the aphid is *Aphis gossypii*; or, alternatively, the nematode is selected from the genus *Meloidogyne* and the aphid is of the genus *Aphis*; or, alternatively, the nematode is selected from the genus *Globodera* and the aphid is of the genus *Aphis*; or, alternatively, the nematode is selected from the genus *Meloidogyne* and the aphid is *Aphis gossypii*; or, alternatively, the nematode is selected from the genus *Globodera* and the aphid is *Aphis gossypii*; or, alternatively, the nematode is selected from the group consisting of *Meloidogyne incognita, Meloidogyne javanica, Globodera rostochiensis* and *Globodera pallida*, and the aphid is of the genus *Aphis*; or, alternatively, the nematode is selected from the group consisting of *Meloidogyne incognita, Meloidogyne javanica, Globodera rostochiensis* and *Globodera pallida*, and the aphid is *Aphis gossypii*.

12. The method according to claim 10, wherein the nematode is a root-knot nematode or a cyst nematode.

13. A kit comprising an effective amount of the composition of claim 1.

* * * * *

SEQUENCE LISTING

```
<160> NUMBER OF SEQ ID NOS: 7

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
agagtttgat cctggctcag                                              20

<210> SEQ ID NO 2
<211> LENGTH: 15
<212> TYPE: DNA
<213> ORGANISM: Artificial Sequence
<220> FEATURE:
```

```
<223> OTHER INFORMATION: Primer

<400> SEQUENCE: 2
accttgttac gactt                                                          15

<210> SEQ ID NO 3
<211> LENGTH: 965
<212> TYPE: DNA
<213> ORGANISM: Artificial Sequence
<220> FEATURE:
<223> OTHER INFORMATION: Amplicon
<220> FEATURE:
<221> NAME/KEY: misc_feature
<222> LOCATION: (130)..(130)
<223> OTHER INFORMATION: n is a, c, g, or t
<220> FEATURE:
<221> NAME/KEY: misc_feature
<222> LOCATION: (145)..(146)
<223> OTHER INFORMATION: n is a, c, g, or t

<400> SEQUENCE: 3
tgcaagtcga gcgaatctga gggagcttgc tcccaaagat tagcggcgga cgggtgagta          60
acacgtgggt aacctgcctg taagattggg ataactccgg gaaaccggag ctaataccgg         120
ataacatttn gaaccgcatg gttcnnaatt gaaagacggc ttttagctgt cacttacaga         180
tggacccgcg gcgcattagc tagttggtga ggtaacggct caccaaggca acgatgcgta         240
gccgacctga gagggtgatc ggccacactg ggactgagac acggcccaga ctcctacggg         300
aggcagcagt agggaatctt ccgcaatgga cgaaagtctg acggagcaac gccgcgtgaa         360
cgatgaaggc cttcgggtcg taaagttctg ttgttaggga agaacaagta ccagagtaac         420
tgctggtacc ttgacggtac ctaaccagaa agccacggct aactacgtgc cagcagccgc         480
ggtaatacgt aggtggcaag cgttgtccgg aattattggg cgtaaagcgc gcgcaggcgg         540
tttcttaagt ctgatgtgaa agcccacggc tcaaccgtgg agggtcattg gaaactgggg         600
aacttgagtg cagaagagga gagtggaatt ccacgtgtag cggtgaaatg cgtagagatg         660
tggaggaaca ccagtggcga aggcgactct ctggtctgta actgacgctg aggcgcgaaa         720
gcgtggggag cgaacaggat tagataccct ggtagtccac gccgtaaacg atgagtgcta         780
agtgttagag ggtttccgcc ctttagtgct gcagcaaacg cattaagcac tccgcctggg         840
gagtacggtc gcaagactga aactcaaagg aattgacggg ggcccgcaca agcggtggag         900
catgtggttt aattcgaagc aacgcgaaga accttaccag gtcttgacat ccttcgctac         960
ttcta                                                                    965

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
cggaatcgct agtaatcgcg                                                     20

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
```

```
cccaatcatc tgtcccacct                                              20

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
tcgggtcgta aagctctgtt                                              20

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
ttctgcactc aagttcccca                                              20
```